US006762343B2

(12) United States Patent
Chu et al.

(10) Patent No.: US 6,762,343 B2
(45) Date of Patent: Jul. 13, 2004

(54) MICE WITH COMBINED DISRUPTION OF GPX1 AND GPX2 GENES HAVE GROWTH RETARDATION, HYPOTHERMIA, AND COLITIS AND PROVIDE A MOUSE MODEL FOR CANCER

(75) Inventors: Fong-Fong Chu, San Gabriel, CA (US); Robert S. Esworthy, San Gabriel, CA (US); James H. Doroshow, Arcadia, CA (US)

(73) Assignee: City of Hope, Duarte, CA (US)

(*) Notice: Subject to any disclaimer, the term of this patent is extended or adjusted under 35 U.S.C. 154(b) by 0 days.

(21) Appl. No.: 10/084,621

(22) Filed: Feb. 28, 2002

(65) Prior Publication Data

US 2003/0009776 A1 Jan. 9, 2003

Related U.S. Application Data

(63) Continuation-in-part of application No. 09/973,196, filed on Oct. 10, 2001, now abandoned.
(60) Provisional application No. 60/238,443, filed on Oct. 10, 2000.

(51) Int. Cl.$^7$ .................... A01K 67/027; C12N 5/00; C11N 5/02
(52) U.S. Cl. .................................. 800/18; 435/325
(58) Field of Search .................. 800/18, 3, 10, 800/13, 22, 25; 435/325

(56) References Cited

PUBLICATIONS

Moreadith et al. Gene targeting embryonic stem cells. J. Mol. Med. 1997, vol. 75, pp. 208–216.*
Moens et al. Defects in heart and lung development in compounds heterozygotes for two different targeted mutations at the N myc locus. Development. 1993, vol. 119, pp. 485–499.*
Seamark et al. Progress and emerging problems in livestock transgenesis: a summary perpective. Reprod. Fertil. Dev. 199 vol. 6, pp. 653–657.*
Mullins et al. Perspective series: molecular medicine in genetically engineered animals. J. Clin. Invest. 1996, vol. 98, No. 11 pp. S37–S40.*
Ursini et al. Dual Function of the Selenoprotein PHGPx . . . , Science, 285:1393–1396, 1999.
Chu et al., "The Human Glutathione Peroxidase Genes GPX2, . . . ,", Cytogenet Cell Genet, 66:96–98, 1994.
Chu et al., "Expression, Characterization, and Tissue Distribution of a New Cellular . . . ,", The Journal of Biological Chemistry, 268(4):2571–2576, 1993.
Esworthy et al., "Selenium–Dependent Glutathione Peroxidase–G1 Is A Major Glutathione . . . ,", Biochimica et Biophysica Acta, 1381:213–226, 1998.
Tham et al., "Expression of Extracellular Glutathione Peroxidase in Human . . . ,", Amer. Physiological Society, 275:G1463–G1471, 1998.

Kim et al., "Increase in Extracellular Glutathione Peroxidase in Plasma . . . ,", Pediatric Research., 46(6):715–721, 1999.
Ho et al., "Mice Deficient in Cellular Glutathione Peroxidase Develop Normally . . . ,", J Biol Chem, 272(26):16644–16651, 1997.
Esposito et al., "Mitochondrial Oxidative Stress in Mice Lacking . . . ,", Free Radical Biology & Medicine, 28(5):754–766, 2000.
Esworthy et al., "Low Glutathione Peroxidase Activity in Gpx1 Knockout Mice . . . ,", Am. J. Physiol Gastrointest Liver Physiol., 279:G426–G436, 2000.
Cheng et al., "Cellular Glutathione Peroxidase Is the Mediator of Body Selenium . . . ," American Society for Nutritional Sciences, 128:1070–1076, 1998.
de Haan et al., "Mice With a Homozygous Null Mutation for the Most Abundant Glutathione . . . ,", The Journal of Biological Chemistry, 273(35):22528–22536, 1998.
Klivenyi et al, "Mice Deficient in Cellular Glutathione Peroxidase Show Increased . . . ,", The Journal of Neuroscience, 20(1):1–7, 2000.
Tipton et al., "Advances in Our Understanding of the Mechanisms of the Neurotoxicity,", Journal of Neurochemistry, 61, 4:1191–206, 1993.
Mirochnitchenko et al., "Thermosensitive Phenotype of Transgenic Mice Overproducing . . . ,", Proc. Natl. Acad. Sci. USA, 92:8120–8124, 1995.
Jiang et al., "Chronic Brain Oxidation in a Glutathione Peroxidase Knockout Mouse . . . ,", Experimental Neurology, 164:257–268, 2000.
Lu et al., "Enhanced Skin Carcinogenesis in Transgenic Mice With High Expression . . . ," Cancer Research, 57:1468–1474, 1997.
Panwala et al., "A Novel Model of Inflammatory Bowel Disease,", Am. Assoc. of Immun., 161: 5733–5744, 1998.
Madsen et al., "Antibiotic Therapy Attenuates Colitis In Interleukin 10 . . . ,", Gastroenterology, 118:1094–1105, 2000.
Thomas et al., "Selenium and Glutathione Peroxidase Status in Pediatric . . . , ", J. Pediatic Gastroenterology and Nutrition, 19:213–219, 1994.

(List continued on next page.)

Primary Examiner—Peter Paras
(74) Attorney, Agent, or Firm—Rothwell, Figg, Ernst & Manbeck

(57) ABSTRACT

Disclosed is a transgenic knockout mouse whose genome has a homozygous disruption in its endogenous Gpx1 and Gpx2 genes, wherein the disruptions result in a decrease in GPX activity in the transgenic mice when compared to non transgenic mice of the same type. Methods for production of the mouse are presented. Also disclosed are cells derived from the transgenic knockout mouse. The invention further provides a mouse model for the disorders of ileitis, colitis, inflammatory bowel disease, ileal cancer and myeloleukemia. The mouse can be used in a method for identifying therapeutic agents for the treatment of an individual diagnosed with one or more of said disorders.

14 Claims, 7 Drawing Sheets

OTHER PUBLICATIONS

Hoffenberg et al., "Circulating Antioxidant Concentrations in Children With . . . ,", *Am J Clin Nutr*, 65:1482–1488, 1997.

Rannem et al., "Selenium Status in Patients with Crohn's Disease,", *Am. J. Clin. Nutr.*, 56:933–937, 1992.

Threadgill, D. W. et al., "Targeted Disruption of Mouse EGF Receptor: Effect of Genetic Background on Mutant Phenotype," *Science* 269:230–234, Jul. 1995.

Macphee, M. et al., "The Secretory Phospholipase A2 Gene is a Candidate for the Mom1 Locus . . . ," *Cell* 81:957–966, Jun. 1995.

Dietrich, W. F. et al., "Genetic Identification of Mom–1, a Major Modifier Locus Affecting Min–Induced Intestinal Neoplasia in the Mouse," *Cell* 75:631–639, Nov. 1993.

"Surviving a Knockout Blow" *Nature*, vol. 415, pp. 8–9, Jan. 3, 2002.

"Intestinal Microflora are Necessary for Development of Spontaneous Adenocarcinoma of the Large Intestine in T–Cell Receptor β Chain and p53 Double–Knockout Mice", *Yakult Central Institute for Microbiological Research*, Cancer Research 61, pp. 2395–2398, Mar. 15, 2001.

"Loss of UCH–L1 and Uch–L3 Leads to Neurodegeneration, Posterior Paralysis and Dysphagia" *Human Molecular Genetics*, 2001, vol. 10, No. 18, pp. 1963–1970, Jun. 2001.

"A Systematic, Genome–wide, Phenotype–driven Mutagenesis Programme for Gene Function Studies in the Mouse", *Nature Genetics*, vol. 25, pp. 440–443, Aug. 2000.

"Genome–wide, Large–scale Production of Mutant Mice by ENU Mutagenesis", *Nature Genetics*, vol. 25, pp. 444–447, Aug. 2000.

"Modifier Genes in Mice and Humans", *Nature Reviews*, vol. 2, pp. 165–174, Mar. 2001.

"Loss of Caveolae, Vascular Dysfunction, and Pulmonary Defects in Caveolin–1 Gene–Disrupted Mice", *Science*, vol. 293, pp. 2449–2452, Sep. 2001.

\* cited by examiner

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: PCR primer mPX101F

<400> SEQUENCE: 1
aaggaggtgc aggcggctgt gagcg                                          25

<210> SEQ ID NO 2
<211> LENGTH: 21
<212> TYPE: DNA
<213> ORGANISM: Artificial Sequence
<220> FEATURE:
<223> OTHER INFORMATION: PCR primerGPX15

<400> SEQUENCE: 2
accgttcacc ttgcacttct c                                              21

<210> SEQ ID NO 3
<211> LENGTH: 26
<212> TYPE: DNA
<213> ORGANISM: Artificial Sequence
<220> FEATURE:
<223> OTHER INFORMATION: PCR primer pPNTpgk

<400> SEQUENCE: 3
cagtttcata gcctgaagaa cgagat                                         26

<210> SEQ ID NO 4
<211> LENGTH: 21
<212> TYPE: DNA
<213> ORGANISM: Artificial Sequence
```

```
<220> FEATURE:
<223> OTHER INFORMATION: PCR primer MPX206

<400> SEQUENCE: 4
cccacctgtc tagaggactt a                                        21

<210> SEQ ID NO 5
<211> LENGTH: 20
<212> TYPE: DNA
<213> ORGANISM: Artificial Sequence
<220> FEATURE:
<223> OTHER INFORMATION: PCR primer MPXin09

<400> SEQUENCE: 5
tccatgccaa cgtagtgatt                                          20
```

MICE WITH COMBINED DISRUPTION OF GPX1 AND GPX2 GENES HAVE GROWTH RETARDATION, HYPOTHERMIA, AND COLITIS AND PROVIDE A MOUSE MODEL FOR CANCER

CROSS REFERENCE TO RELATED APPLICATION

This application is a Continuation-in-part of application No. 09/973,196, filed Oct. 10, 2001 now abandoned which is related to provisional application No. 60/238,443 filed Oct. 10, 2000.

The publications and other materials used herein to illuminate the background of the invention or provide additional details respecting the practice are incorporated by reference.

TECHNICAL FIELD OF THE INVENTION

The present invention is directed towards specific double knockout(DKO) animals and their use as animal models. More specifically, the double knockout animals contain a disruption in the genes encoding GPX-1 and GPX-GI. Corresponding cells which are amenable to tissue culture are also part of the invention, as are methods of using such cells, including their use as a tool for identifying therapeutic agents. In addition, the invention is directed towards a mouse model of cancer of the small bowel.

BACKGROUND OF THE INVENTION

Selenium-dependent glutathione peroxidases (GPXs) are a family of enzymes that are most efficient in the reduction of hydroperoxides. At the present time there are four known selenoproteins with GPX activity. These include the classical ubiquitous GPX-1, GPX-GI, the secreted GPX-P, and PHGPX (Ursini, F., Heim, S., Kiess, M., Maiorino, M., Roveri, A., Wissing, J. & Flohe, L. (1999) Science 285, 1393–6). These GPX isozymes are encoded by four distinct genes, the Gpx1 gene for GPX-1, the Gpx2 gene for GPX-GI, the Gpx3 gene for GPX-P, and the Gpx4 gene for PHGPX (Chu, F. F. (1994) Cytogenet Cell Genet 66, 96–8). The GPX-1 and GPX-GI isozymes have very similar properties including substrate specificity and cytosolic localization (Chu, F. F., Doroshow, J. H. & Esworthy, R. S. (1993) J. Biol Chem 268, 2571–6; Esworthy, R. S., Swiderek, K. M., Ho, Y. S. & Chu, F. F. (1998) Biochim Biophys Acta 1381,213–26). The unique feature of GPX-GI is its high levels of expression in the epithelium of the GI-tract. GPX-P is found in body fluids such as plasma, lung and GI-tract (Tham, D. M., Whitin, J. C., Kim, K. K., Zhu, S. X. & Cohen, H. J. (1998) Am J Physiol 275, G1463–71; Kim, K. K., Whitin, J. C., Sukhova, N. M. & Cohen, H. J. (1999) Pediatr Res 46, 715–21). PHGPX is present at a high level in testis and is implicated in sperm maturation (1, Roveri, A., Casasco, A., Maiorino, M., Dalan, P., Cafligaro, A. & Ursini, F. (1992) J Biol Chem 267, 6142–6). PHGPX is present in low level in the GI-tract (Chu, F. F. & Esworthy, R. S. (1995) Arch. Biochem. Biophys. 323, 288–94). Both GPX-P and PHGPX can reduce phospholipid and cholesterol hydroperoxides, while the latter is a more efficient enzyme at reducing these substrates (Thomas, J. P., Maiorino, M., Ursini, F. & Girotti, A. W. (1990) J. Biol. Chem. 265, 454–6 1; Esworthy, R. S., Chu, F. F., Geiger, P., Girotti, A. W. & Doroshow, J. H. (1993) Arch. Biochem. Biophys. 307, 29–34).

It is known that knockout (KO) mice homozygous for disruption of single Gpx1 and Gpx2 genes (i.e., Gpx1-KO and Gpx2-KO mice) display little pathology without additional stress (Ho, Y. S., Magnenat, J. L., Bronson, R. T., Cao, J., Gargano, M., Sugawara, M. & Funk, C. D. (1997) J. Biol. Chem. 272, 16644–51; Esposito, L. A., Kokoszka, J. E., Waymire, K. G., Cottrell, B., MacGregor, G. R. & Wallace, D.C. (2000) Free Radic. Biol. Med. 28, 754–66; Esworthy, R. S., Mann, J. R., Sam, M. & Chu, F. (2000) Am. J. Physiol. Gastrointest. Liver Physiol. 279, G426–G436.). However, aged Gpx1-KO mice display spontaneous weight loss (Esposito, L. A., Kokoszka, J. E., Waymire, K. G., Cottrell, B., MacGregor, G. R. & Wallace, D.C. (2000) Free Radic. Biol. Med. 28, 754–66). For example, the Gpx1 gene is expressed ubiquitously and is highly expressed in the erythrocyte, liver, and kidney. The antioxidant function of GPX-1 is revealed in Gpx1-KO mice especially after treatment with prooxidant chemicals. An increased level of $H_2O_2$ is produced from liver mitochondria in older (5–6 month) Gpx1-KO mice compared with that from wildtype mice without any treatment. GPX-1 can prevent lipid peroxidation induced by paraquat herbicide or measured in liver and lung and protect cortical neurons against $H_2O_2$ (Cheng, W. H., Ho, Y. S., Valentine, B. A., Ross, D. A., Combs, G. F., Jr. & Lei, X. G. (1998) J. Nutr. 128,1070–6; de Haan, J. B., Bladier, C., Griffiths, P., Kelner, M., O'Shea, R. D., Cheung, N. S., Bronson, R. T., Silvestro, M. J., Wild, S., Zheng, S. S., Beart, P. M., Hertzog, P. J. & Kola, 1. (1998) J. Biol. Chem. 273, 22528–36). The Gpx1-KO mice are more susceptible to neurotoxic agents as malonate, 3-nitropropionic acid, and 1-methyl-4-phenyl-1,2,5,6-tetrahydropyridine (MPTP) in the brain (Klivenyi, P., Andreassen, O. A., Ferrante, R. J., Dedeoglu, A., Mueller, G., Lancelot, E., Bogdanov, M., Andersen, J. K., Jiang, D. & Beal, M. F. (2000) J. Neurosci. 20, 1–7). Malonate induces hydroxyl radical generation while MPP+, the active metabolite of MPTP, inhibits mitochondrial complex I activity (Tipton, K. F. & Singer, T. P. (1993) J Neurochem 61, 1191–206). Since these neurotoxins produce oxidative stress and impair energy production, GPX-1 is implicated in protection against oxidative damage.

Depending on the type of insult, lack of GPX activity can also be beneficial under certain circumstances. Mice overexpressing GPX-1 and GPX-P have low levels of peroxides and prostaglandins and are more sensitive to hyperthermia (Mirochnitchenko, O., Palnitkar, U., Philbert, M. & Inouye, M. (1995) Proc. Natl. Acad. Sci. USA 92, 8120–4). We have found that the jejunum crypt of Gpx1-KO mice regenerates better than that in the wildtype after exposure to high dose γ-irradiation (Esworthy, R. S., Mann, J. R., Sam, M. & Chu, F. (2000) Am J Physiol Gastrointest Liver Physiol 279, G426). Perhaps the higher level of GPX-GI in the Gpx1-KO mouse intestine are directly responsible for crypt regeneration. Furthermore, the lack of GPX activity in the Gpx1-KO mouse can be protective against kainic acid-induced limbic seizures and neurodegeneration (Jiang, D., Akopian, G., Ho, Y. S., Walsh, J. P. & Andersen, J. K. (2000) Exp. Neurol. 164, 257–68). This appears to result from decreased receptor function for N-methyl-D-aspartate (NMDA), since kainic acid induces NMDA-dependent seizure. Increased GPX activity in mice overexpressing the Gpx1 gene may have enhanced carcinogenic response in skin treated with 7,12-dimethylbenz[a]anthracene and 2-0-tetradecanoylphorbol-13-acetate (Lu, Y. P., Lou, Y. R., Yen, P., Newmark, H. L., Nfirochnitchenko, 0. I., Inouye, M. & Huang, M. T. (1997) Cancer Res. 57, 1468–74). The mechanism of the pro-carcinogenic activity is not known but it is apparent that elevated antioxidant activity can be debilitating, depending on the type of insult.

GPX activity is also implicated in protection against infectious agents. For example, Jaeschke et al. have found that Gpx1-KO mice are more susceptible to neutrophil-mediated parenchymal cell injury during endotoxemia (Jaeschke, H., Ho, Y. S., Fisher, M. A., Lawson, J. A. & Farhood, A. (1999) Hepatology 29,443–50). The galactosamine/endotoxin induced acute liver failure involves neutrophils and GPX protects hepatocytes against peroxides generated by infiltrated neutrophils in the liver. It has also previously been shown that Gpx1-KO mice are more susceptible to coxsackievirus-induced myocarditis (Beck, M. A., Esworthy, R. S., Ho, Y. S. & Chu, F. F. (1998) Faseb J. 12,1143–9). Viral antibody titers in the Gpx1-KO mice are less than 20% of those found in the wildtype mice, suggesting that cellular immune response is impaired in the Gpx1-KO mice.

Gpx2-KO mice have also recently been generated and these mice appear to be normal (Esworthy et al., Am. J. Physiol. Gastrointest. Liver Physiol. 279, G426–G436). Unlike the Gpx1 gene, which is expressed ubiquitously, the Gpx2 gene is expressed specifically in epithelium. The Gpx2 gene is highly expressed in the gastrointestinal tract, and is also present in the breast, lung, and human liver (Chu, F. F., Doroshow, J. H. & Esworthy, R. S. (1993) J. Biol. Chem. 268, 2571–6; Chu, F. F., Esworthy, R. S., Lee, L. & Wilczynski, S. (1999) J. Nutr. 129, 1846–1854). In the GI-epithelium, GPX-1 and GPX-GI contribute to most of GPX activity (Esworthy, R. S., Swiderek, K. M., Ho, Y. S. & Chu, F. F. (1998) Biochim. Biophys. Acta. 1381,213–26.). The lack of pathology in Gpx2-KO mice is not unexpected, since the Gpx2 gene has limited tissue expression, the Gpx1 gene is co-expressed in tissues expressing the Gpx2 gene, and GPX-1 and GPX-GI have similar biochemical and cellular properties.

Reactive oxidative species are implicated to play an important role in the pathogenesis of inflammatory bowel disease (IBD), which is caused, at least in part, by bacterial infection (Panwala, C. M., Jones, J. C. & Viney, J. L. (1998) J Immunol 161, 5733–44; Madsen, K. L., Doyle, J. S., Tavernini, M. M., Jewell, L. D., Rennie, R. P. & Fedorak, R. N. (2000) Gastroenterology 118, 1094–105; Sands, B. E. (2000) Gastroenterology 118, S68–82). IBD consists of two disorders that have similar symptoms, i.e., ulcerative colitis and Crohn's disease. Although elevated $H_2O_2$ is detected in IBD (Simmonds, N. J., Allen, R. E., Stevens, T. R., Van Someren, R. N., Blake, D. R. & Rampton, U. S. (1992) Gastroenterology 103, 186–96; Keshavarzian, A., Sedghi, S., Kanofsky, J., List, T., Robinson, C., Ibrahim, C. & Winship, D. (1992) Gastroenterology 103,177–85)., the protective effect of GPX against IBD has not yet been established. Elevated GPX activity in red blood cells and/or plasma found in IBD patients is implicated against the protective role of GPX in IBD (Thomas, A. G., Miller, V., Shenkin, A., Fell, G. S. & Taylor, F. (1994) J. Pediatr. Gastroenterot. Nutr. 19, 213–9; Offenberg, E. I., Deutsch, J., Smith, S. & Sokol, R. J. (1997) Am J Clin Nutr 65, 1482–8. 31. Rannem, T., Ladefoged, K., Hylander, E., Hegnhoj, J. & Jarnum, S. (1992) Am. J. Clin. Nutr. 56, 933–7). Although selenium-deficiency is commonly present in those patients with severe gastrointestinal disorders (31; Rannem, T., Ladefoged, K., Hylander, E., Hegnhoj, J. & Staun, M. (1998) Scand J Gastroenterol 33, 1057–61), this is believed to result from IBD rather than contributing to IBD.

The evaluation of chemical compounds for potential efficacy as human therapeutics necessitates data and information of a compound's efficacy in vivo. Ideally, the in vivo system would be human but ethical and pragmatic reasons prevent such data from being accumulated. As an alternative, many laboratory animals provide satisfactory systems for screening potential therapeutics for treating human physiological disorders. Recent advances in recombinant DNA technology have enabled researchers to genetically manipulate the genomes of animals to enhance such animal model systems. For example, the technique of transgenic generation have been utilized to produce knockout mice that do not express a particular endogenous gene.

There presently exists a need for animal models which can be utilized to study the physiological function of GPX activity in the GI-tract. One approach to generate a useful model for such studies would be double knockout (double-KO) mice with a combined disruption of both alleles of each of the Gpx1 and Gpx2 genes.

SUMMARY OF THE INVENTION

In accordance with the present invention, an animal model is provided for studying the significance of GPX-1 and GPX-GI, in particular with regard to how these two gene products interact in animal physiology.

In one aspect, the invention provides a transgenic animal deficient in both GPX-1 and GPX-GI activity. In a preferred embodiment, the animal is a mouse. The deficiency is a result of a homozygous double knockout of the Gpx1 and Gpx2 genes in said transgenic mouse.

In another aspect, the invention provides an animal model for the study of pathophysiological function of GPX activity in the ileum and colon in mammals. We have found that the homozygous double-KO mice of the present invention can exhibit symptoms associated with ileitis, colitis, growth retardation, hypothermia, wasting syndrome, inflammatory bowel disease, cancer in the lower GI-tract and leukemia.

In one aspect, the invention provides an animal model for the study of the degree of functional redundancy of GPX-1 and GPX-GI in the ileum and colon in mammals.

In one embodiment, the invention provides transgenic mice which have a homozygous knockout of the Gpx1 gene in said transgenic mice, together with a heterozygous knockout of one allele of the Gpx2 gene. The invention thus provides an animal model for the study of the degree of functional redundancy of GPX-1 and GPX-GI in the ileum and colon.

In another embodiment, the invention provides transgenic mice which have a homozygous knockout of the Gpx2 gene, together with a heterozygous knockout of one allele of the Gpx1 gene in said transgenic mice. The invention thus provides another animal model for the study of the degree of functional redundancy of GPX-1 and GPX-GI in the ileum and colon.

In another embodiment, the invention provides a transgenic double knockout mouse whose genome comprises a homozygous disruption of the endogenous Gpx1 gene and a homozygous disruption of the endogenous Gpx2 gene (a transgenic double knockout Gpx1/Gpx2 mouse), wherein each disruption comprises the insertion of a transgene, and wherein the combined disruptions result in a decreased level of GPX-1 and GPX-GI production and decreased number of cells producing GPX-I and GPX-GI in the transgenic mouse as compared to a nontransgenic mouse.

In another embodiment, the invention provides a transgenic double knockout Gpx1/Gpx2 mouse which exhibits a physiological disease, symptom or symptoms selected from the group consisting of ileitis, colitis, hypothermia, decreased rate of weight gain, perianal ulceration, diarrhea, wasting syndrome, inflammatory bowel disease, cancer of the ileum and myeloleukemia.

In another embodiment, the invention provides a cell or cells isolated from any of the following: a double knockout Gpx1/Gpx2 transgenic mouse, a transgenic mouse having a heterozygous knockout of the Bpx1 gene and a heterozygous knockout of the Gpx2 gene, a transgenic mouse having a homozygous knockout of the Gpx1 gene and a heterozygous knockout of one allele of the Gpx2 gene and a transgenic mouse having a homozygous knockout of the Gpx2 gene and a heterozygous knockout of one allele of the Gpx1.

In one embodiment, the invention provides a transgenic double knockout Gpx1/Gpx2 mouse which further comprises a mouse which is germ free.

In another embodiment, the invention provides the double knockout of the Gpx1 and Gpx2 genes in mice having different genetic backgrounds. The invention thus provides means to identify other genes that affect the severity of ileitis, colitis, inflammatory bowel disease symptoms and progression to cancer.

In another embodiment, the invention provides the double knockout of the Gpx1 and Gpx2 genes in a genetic background of a B6 mouse.

In another aspect, the invention provides a method of selecting an agent for treating a metabolic disorder selected from the group consisting of: ileitis, colitis, hypothermia, decreased rate of weight gain, perianal ulceration, diarrhea, wasting syndrome, inflammatory bowel disease, ileal cancer and myeloleukemia comprising:

(a) measuring a symptom in a knockout mouse whose genome is manipulated to comprise a homozygous disruption of both the endogenous Gpx1 and Gpx2 genes, wherein the disruption of both the Gpx1 and Gpx2 genes results in said knockout mouse exhibiting one of said disease, symptom or symptoms;

(b) administering an agent to said mouse;

(c) measuring one or more of said symptoms in the mouse after administering the agent; and (d) comparing at least one of said symptoms in the mouse before and after administering the agent, wherein a decrease in said disease, symptom or symptoms after administering the agent indicates the agent is an agent for treating said disease, symptom or symptoms associated with a metabolic disorder.

In another embodiment, the method of observing the effects of treatment of a disease, symptom or symptoms in double-KO Gpx1 and Gpx2 transgenic mice by administering an agent is observed and compared in double-KO Gpx1 and Gpx2 mice having different genetic backgrounds. The method comprises:

(a) measuring a symptom in a first double knockout mouse having a first genetic background, whose genome is manipulated to comprise a homozygous disruption of both the endogenous Gpx1 and Gpx2 genes, wherein the disruption of both the Gpx1 and Gpx2 genes results in said knockout mouse exhibiting a disease, symptom or symptoms selected from the group consisting of: ileitis, colitis, hypothermia, decreased rate of weight gain, perianal ulceration, diarrhea, wasting syndrome, inflammatory bowel disease, ileal cancer and myeloleukemia;

(b) measuring said symptom in a second double knockout mouse having a second genetic background, whose genome is manipulated to comprise a homozygous disruption of both the endogenous Gpx1 and Gpx2 genes, wherein the disruption of both the Gpx1 and Gpx2 genes results in said knockout mouse exhibiting at least one of said disease, symptom or symptoms;

(c) administering an agent to said first and second mouse;

(d) measuring one or more of said symptoms in the first and second mouse after administering the agent; and (e) comparing at least one of said symptoms in said first and second mouse before and after administering the agent, wherein a decrease in said disease, symptom or symptoms after administering the agent indicates the agent is an agent for treating said disease, symptom or symptoms associated with a metabolic disorder.

In another embodiment, the invention provides a method of observing the effects of treatment of a disease, symptom or symptoms in single and Gpx 1/Gpx 2 double knockout transgenic mice in mice with a B6 genetic background or in hybrid mice having a ½ B6, ¼ 129 SvJ and ¼ 129S3 genetic background.

In another embodiment, the invention provides a method of selecting an agent that modulates GPX enzyme activity comprising:

(a) administering an agent to a first group of isolated mouse intestinal epithelial cells and not to a second group of mouse intestinal epithelial cells, wherein the genome of both the first and second isolated mouse cell groups has been manipulated to comprise a homozygous disruption of both alleles of the endogenous Gpx1 gene and Gpx2 genes, and wherein the homozygous disruption of both the endogenous Gpx1 gene and Gpx2 genes prevents expression of functional GPX proteins; and (b) determining the amount of GPX enzyme activity of the first and second cell groups, wherein a difference in the amount of proliferation of the first cell group as compared to the second cell group indicates that the agent modulates GPX enzyme activity. In another embodiment the isolated cells can be observed for a change in level of expression of a marker associated with cancer.

In another embodiment, the invention provides a transgenic animal whose genome contains a homozygous disruption of both the endogenous Gpx1 gene and Gpx2 genes, wherein said animal develops cancer.

In another embodiment, the invention provides an animal model for the development of ileitis, colitis, inflammatory bowel disease, ileal cancer and or myeloleukemia. The model comprises a transgenic animal whose genome comprises a homozygous disruption of the endogenous Gpx1 gene and a homozygous disruption of the endogenous Gpx2 gene, wherein disruption of the Gpx1 and Gpx2 genes is sufficient to effect one or more signs or symptoms in the animal associated with ileitis, colitis, inflammatory bowel disease, ileal cancer and or myeloleukemia.

The invention further provides a method to screen for potential therapeutic agents for the treatment of ileitis, colitis, inflammatory bowel disease, ileal cancer and or myeloleukemia. The method comprises the steps of: a) administering a potential therapeutic agent to a first transgenic animal whose genome comprises a homozygous disruption of both the endogenous Gpx1 gene and Gpx2 genes; b) maintaining the animal for a time sufficient to permit the detection of a change in one or more signs or symptoms in the animal associated with ileitis, colitis, inflammatory bowel disease, ileal cancer and or myeloleukemia in the transgenic animal; c) observing the animal for a change in at least one sign or symptom associated with ileitis, colitis, inflammatory bowel disease, ileal cancer and or myeloleukemia, wherein a second transgenic animal having the same genetic background as the first transgenic animal and whose genome also comprises a homozygous disruption of both the endogenous Gpx1 gene and Gpx2 genes has been maintained under the same conditions as the first animal but has not received the potential therapeutic agent; and d) determining whether one or more signs or symptoms associated with ileitis, colitis, inflammatory bowel disease, ileal cancer and or myeloleukemia is present in the second transgenic animal but not in the first transgenic animal; wherein a potential therapeutic agent will be one that causes a lower incidence of at least one sign or symptom associated with ileitis, colitis, inflammatory bowel disease, ileal cancer and or myeloleukemia in the first transgenic animal.

The invention further provides a method to screen for potential therapeutic agents for the treatment of ileitis, colitis, inflammatory bowel disease, ileal cancer and or myeloleukemia. The method comprises the steps of: a) administering a potential therapeutic agent to an isolated first cell from a first transgenic animal whose genome comprises a homozygous disruption of both the endogenous Gpx1 gene and Gpx2 genes; b) maintaining the cell for a time sufficient to permit the detection of a change in one or more signs or symptoms in the first cell associated with ileitis, colitis, inflammatory bowel disease, ileal cancer and or myeloleukemia in the first cell; c) observing the first cell for a change in at least one sign or symptom associated with ileitis, colitis, inflammatory bowel disease, ileal cancer and or myeloleukemia, wherein a second cell from a second transgenic animal having the same genetic background as the first transgenic animal and whose genome also comprises a homozygous disruption of both the endogenous Gpx1 gene and Gpx2 genes has been maintained under the same conditions as the first cell but has not been exposed to the potential therapeutic agent; and d) determining whether one or more signs or symptoms associated with ileitis, colitis, inflammatory bowel disease, ileal cancer and or myeloleukemia is present in the second transgenic cell but not in the first transgenic cell; wherein a potential therapeutic agent will be one that causes a lower incidence of at least one sign or symptom associated with ileitis, colitis, inflammatory bowel disease, ileal cancer and or myeloleukemia in the first transgenic cell.

The invention further provides a method for assessing the therapeutic effect of a heterologous gene of interest on the development of ileitis, colitis, inflammatory bowel disease, ileal cancer and or myeloleukemia, which comprises the steps of: expressing a heterologous gene of interest in a first transgenic animal whose genome comprises a homozygous disruption of both the endogenous Gpx1 gene and Gpx2 genes; maintaining the first transgenic animal for a time sufficient to permit the detection of one or more signs or symptoms in the first transgenic animal associated with ileitis, colitis, inflammatory bowel disease, ileal cancer and or myeloleukemia in the first transgenic animal; observing the first transgenic animal for a change in at least one sign or symptom associated with ileitis, colitis, inflammatory bowel disease, ileal cancer and or myeloleukemia, wherein a second transgenic animal comprising a homozygous disruption of both the endogenous Gpx1 gene and Gpx2 genes does not express the gene of interest, wherein the second transgenic animal has been maintained under the same conditions as the first transgenic animal; and determining whether one or more signs or symptoms associated with ileitis, colitis, inflammatory bowel disease, ileal cancer and or myeloleukemia is present in the second animal, wherein a gene of interest which reduces the sign or symptom will be one that causes a lower incidence of at least one sign or symptom associated with ileitis, colitis, inflammatory bowel disease, ileal cancer and or myeloleukemia in the first animal.

The invention further provides a method of identifying one or more marker genes or proteins associated with ileal cancer and or myeloleukemia, which comprises the steps of: expressing the marker gene or protein in a first transgenic animal whose genome comprises a homozygous disruption of both the endogenous Gpx1 gene and Gpx2 genes; maintaining the first transgenic animal for a time sufficient to permit the detection a change in one or more signs or symptoms in the first transgenic animal associated with ileitis, colitis, inflammatory bowel disease, ileal cancer and or myeloleukemia in the first transgenic animal; observing the first transgenic animal for a change in at least one sign or symptom associated with ileitis, colitis, inflammatory bowel disease, ileal cancer and or myeloleukemia, wherein a second transgenic animal comprising a homozygous disruption of both the endogenous Gpx1 gene and Gpx2 genes does not express the marker gene or protein, wherein the second transgenic animal has been maintained under the same conditions as the first transgenic animal; and determining whether one or more signs or symptoms associated with ileitis, colitis, inflammatory bowel disease, ileal cancer and or myeloleukemia is present in the first transgenic animal, wherein a marker gene or protein associated with ileitis, colitis, inflammatory bowel disease, ileal cancer and or myeloleukemia will be one that causes a higher incidence of at least one sign or symptom associated with ileitis, colitis, inflammatory bowel disease, ileal cancer and or myeloleukemia in the first animal.

In particularly preferred embodiments, the first and second transgenic animals utilized in the methods of the invention are mice.

DETAILED DESCRIPTION OF THE INVENTION

Figure 1A:
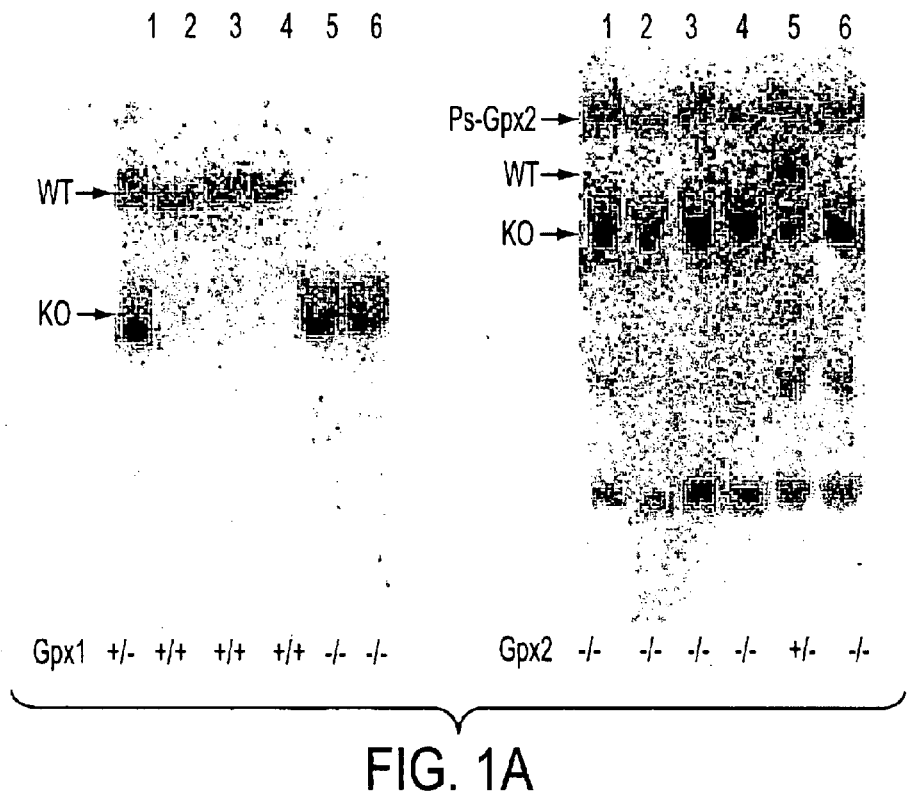
FIG. 1A depicts the results of Southern analysis of various Gpx1 and Gpx2 genes in knockout mice.

The invention provides a transgenic animal whose genome contains a homozygous disruption of both the endogenous Gpx1 gene and Gpx2 genes wherein said animal develops a sign or symptom selected from the group consisting ileitis, colitis, hypothermia, decreased rate of weight gain, perianal ulceration, diarrhea, wasting syndrome, inflammatory bowel disease, ileal cancer and myeloleukemia. In a preferred embodiment, the transgenic animal is a mouse. In another preferred embodiment, the invention provides a model for a sign or symptom associated with ileitis, colitis, hypothermia, decreased rate of weight gain, perianal ulceration, diarrhea, wasting syndrome, inflammatory bowel disease, ileal cancer and myeloleukemia. The transgenic mouse can for example have a genetic background selected from the group consisting of a B6 mouse, a C57B16/J hybrid and a 129Sv/J hybrid mouse. Using techniques well known in the art and described elsewhere (Esworthy et al. (2000) Am J Physiol Gastrointest Liver Physiol 279, G426–G436), a hybrid mouse having a homozygous disruption in a gene or genes can be maintained by inbreeding. Alternatively, hybrid mice having a homozygous or heterozygous disruption in a gene or genes are bred with one of the hybrid's parent strains to generate a subline wherein the mice have a homozygous disruption in a gene or genes in a genetic background for one or the other of the parent strains. In general, generation and maintenance of Gpx1 and Gpx2 homozygous double-KO mice was performed as described in Esworthy et al., Am. J. Physiol.Gastrointest. Liver Physiol. 281:G848–855 (2001).

In a preferred embodiment, the double KO mice of the invention are ½ B6, ¼ 129Sv/J and ¼ 129S3. B6 and 129Sv/J hybrids having a homozygous disruption of the Gpx1 gene are crossed to B6 and 129S3 hybrids having a homozygous disruption of the Gpx2 gene to produce Gpx1 and Gpx2 homozygous double-KO mice that are ½ B6, ¼ 129Sv/J and ¼ 129S3.

C57BL6/J(B6) and 129v/J hybrids mice as described previously (Ho, et al. J. Biol. Chem. 272, 16644–51(1997)) having a Gpx1 knockout were backcrossed to B6 mice for 7 generations, producing mice greater than 90% B6 in genetic background. B6 and 129S3 hybrids (Esworthy et al. Am. J. Physiol. Gastrointest. Liver Physiol. 279, G426–G436 (2000)) having a Gpx2 knockout were also backcrossed to B6 mice for 7 generations. The resulting Gpx1 gene and Gpx2 knockout mice in a B6 background were crossed to produce double knockout mice in a greater than 90% B6 background. Two resultant double KO B(6) mice had ileitis and colitis.

The transgenic animal of the invention provides an animal model for ileal cancer and or myeloleukemia. In a preferred embodiment, the model comprises a transgenic mouse whose genome contains a homozygous disruption of both the endogenous Gpx1 gene and Gpx2 genes wherein said animal develops one or more signs or symptoms of cancer of ileal cancer and or myeloleukemia. The transgenic mouse of the invention displays at least one sign or symptom associated with cancer is selected from the group consisting of ileitis, colitis, hypothermia, decreased rate of weight gain, perianal ulceration, diarrhea, wasting syndrome, inflammatory bowel disease, one or more tumors in the small bowel and myeloleukemia. In one embodiment, the transgenic mouse of the invention can further comprise a mouse which is a germ free mouse.

In another embodiment, the invention provides a method to screen for potential therapeutic agents for the treatment of ileal cancer and or myeloleukemia. A potential therapeutic agent is administered to a first transgenic animal whose genome comprises a homozygous disruption of both the endogenous Gpx1 gene and Gpx2 genes. The first transgenic animal is maintained for a time sufficient to permit the detection of a change in one or more signs or symptoms of ileal cancer and or myeloleukemia in the transgenic animal. A second transgenic animal having the same genetic background as the first transgenic animal and whose genome also comprises a homozygous disruption of both the endogenous Gpx1 gene and Gpx2 genes is maintained under the same conditions as the first animal but does not receive the potential therapeutic agent. The first and second animals are observed for a change in at least one sign or symptom associated with ileal cancer and or myeloleukemia. A therapeutic agent which prevents one or more signs or symptoms of ileal cancer and or myeloleukemia in the first transgenic animal when compared to the second transgenic animal will be a potential therapeutic agent for the treatment or prevention of ileal cancer and or myeloleukemia. In a preferred embodiment, the sign or symptom of ileal cancer is the development of tumors in the distal two thirds of the small intestine. In a preferred embodiment, detection of tumors in the small bowel of the animal is performed by sacrificing the first and second animal after a time sufficient for the detection of at least one tumor of the small bowel in the first and second animals has elapsed and observing the tissue of the small bowel using techniques well known in the art. In another preferred embodiment, the transgenic animal is a mouse. In one embodiment, the mouse has a B6 genetic background. In yet another preferred embodiment, the mouse has a genetic background of ½ B6, ¼ 129Sv/J and ¼ 129S3.

In another embodiment, a potential therapeutic agent is administered to a first transgenic animal whose genome comprises a homozygous disruption of both the endogenous Gpx1 gene and Gpx2 genes and to a second transgenic animal having a different genetic background from the first transgenic animal and whose genome also comprises a homozygous disruption of both the endogenous Gpx1 gene and Gpx2 genes and the effects of the therapeutic agent on the development of ileal cancer and or myeloleukemia is compared in the two animals.

Many signs or symptoms associated with ileal cancer and or myeloleukemia are known in the art which may be used to screen for the development of ileal cancer or myeloleukemia. Some non-limiting examples include ileitis, colitis, inflammatory bowel disease, the appearance of areas of dysplasia in epithelial cells of the small intestine, tumors in the small intestine, the presence of abnormal telomerase activity in cells, exfoliated cancer cells in stool and the presence of antibody to small intestine mucin antigen. Thus, in some embodiments, the animals do not have to be sacrificed to detect a sign or symptom associated with cancer.

It is contemplated that other methods of detecting the tumors or other signs or symptoms of cancer can be substituted for microscopic examination of tissue without departing from the scope of the invention. Non limiting examples may include withdrawing a body fluid from the first and second animal and analyzing the body fluid such as blood, for example, for the presence of one or more signs or symptoms of cancer of the ileum. By way of example, exfoliated cancer cells in stool or blood samples could be examined for reaction with antibody for small intestine mucin antigen or by PCR telomerase reactions, as known by those skilled in the art. See, e.g., Pinczower, et al., International. J. Cancer 54(3) 391–396 (1993); Guadagni et al., Cancer Res. 56(22):5293–5299; and Gauthier et al., Br. J. Cancer 84(5) 631–635 (2001).

The invention further provides a transgenic animal whose genome comprises a homozygous disruption of both the endogenous Gpx1 gene and Gpx2 genes wherein the animal's genome can additionally comprise a DNA sequence encoding a heterologous gene of interest. The gene of interest may code for a biologically active nucleic acid or polypeptide including, for example, an an immunomodulator, a peptide, an oligonucleotide and the like. The gene of interest can also be inserted within a target gene of the transgenic animal of the invention in order to disrupt that target gene, thereby generating a knockout mouse having a homozygous disruption of the Gpx1, Gpx2 and target genes. The heterologous gene of interest can comprise, for example, an antibiotic marker gene or an allelic variant of the gene to be disrupted, wherein the allelic variant is not expressed or is not biologically active. In addition, genes can be disrupted by providing an antisense RNA, a ribozyme and the like to prevent transcription or translation of the target gene.

The invention further provides a method for assessing the therapeutic effect of a heterologous gene of interest on the development of ileal cancer and or myeloleukemia which comprises expressing the heterologous gene of interest in a first transgenic animal whose genome comprises a homozygous disruption of both the endogenous Gpx1 gene and Gpx2 genes. The first transgenic animal is maintained for a time sufficient to permit the detection a change in one or more signs or symptoms in the first transgenic animal associated with ileal cancer and or myeloleukemia. A second transgenic animal having the same genetic background as the first transgenic animal and comprising a homozygous disruption of both the endogenous Gpx1 gene and Gpx2 genes which does not express the gene of interest is maintained under the same conditions as the first transgenic animal. Both transgenic animals are observed for the presence or absence of one or more signs or symptoms of ileal cancer and or myeloleukemia.

In another embodiment, a heterologous gene of interest can be expressed in a first transgenic animal whose genome comprises a homozygous disruption of both the endogenous Gpx1 gene and Gpx2 genes. The heterologous gene of interest is not expressed in a second animal having a homozygous disruption in both the endogenous Gpx1 gene and Gpx2 genes but the first and second animals have different genetic backgrounds.

The invention further provides a method of identifying markers associated with ileitis, colitis, inflammatory bowel disease, ileal cancer and or myeloleukemia, the method comprising comparing the presence, absence or level of expression of at least one gene or protein in a transgenic animal whose genome comprises a homozygous disruption of both the endogenous Gpx1 gene and Gpx2 genes with the level or expression of the gene or protein in a second animal, wherein the second animal has the same genetic background as the first animal but does not comprise a homozygous disruption of both the endogenous Gpx1 gene and Gpx2 genes, wherein the difference between the first transgenic animal and the second animal in the presence, absence or level of expression of the gene or protein indicates that the expression of the gene is a marker associated with cancer of the small bowel.

The invention further provides cells isolated from the knockout mice of the invention. Such cells can be of any cell type that can be isolated from the transgenic animal, utilizing techniques well known in the art. By way of example, isolated cells can include stem cells, epithelial cells, myofibroblasts and the like. The cells can be utilized in in vitro experiments to study the physiologic characteristics of such cells and can comprise cell lines from the knockout mice.

General Methods

The practice of the present invention employs, unless otherwise indicated, conventional techniques of chemistry, molecular biology, microbiology, recombinant DNA, genetics, immunology, cell biology, cell culture and transgenic biology, which are known to one of ordinary skill in the related art.

Gpx1-KO mice were generated by using standard techniques as C57BL6/J (B6) and 129Sv/J hybrids and B6 inbred mice as described previously (Ho, Y. S., Magnenat, J. L., Bronson, R. T., Cao, J., Gargano, M., Sugawara, M. & Funk, C. D. (1997) J Biol Chem 272, 16644–51).

The generation of Gpx2-KO mice as B6 and 129S3 hybrids and B6 mice has been described previously (Esworthy, R. S., Mann, J. R., Sam, M. & Chu, F. (2000) Am J Physiol Gastrointest Liver Physiol 279, G426–G436). These mice were housed in ventilated cage racks (Allentown Caging Equipment, Allentown, N.J.) under conventional housing conditions. The colony was monitored for infectious pathogens via sentinel mouse surveillance and necropsy of randomly selected littermates of the double-KO mice. The loose stools of several double-KO mice were negative for parasites. All mice had free access to laboratory rodent diet (5001, Purina Mills Inc., Richmond, Ind.) and water. This diet contains 23% protein, 4.5% fat, 6% fiber, and 0.28 ppm selenium as provided by the manufacturer (LabDiet).

Genotyping of Gpx1 and Gpx2-KO mice was done with either Southern or PCR analysis of DNA isolated from tails. For Southern analysis, 10 μg DNA was digested with BamHI or ApaI to determine the genotype of Gpx1 and Gpx2, respectively. After overnight digestion, DNA was resolved in 0.75% agarose gel and transferred to Zeta Probe membrane (BioRad Lab., Richmond, Calif.) and probed with $^{32}$P-labeled and random-primed 3' EcoRi fragment of mouse Gpx1 cDNA and mouse Gpx2 exon 2 CDNA. The Southern blot was analyzed by phosphor imaging (Molecular Dynamics, Sunnyvale, Calif.) (13). Polymerase Chain Reactions (PCR) were also performed. The PCR primers for the wildtype Gpx1 allele were mPX101F (DNA SEQ ID NO. 1:5'-AAGGAGGTGCAGGCGGCTGTGAGCG-3') and GPX15 (SEQ ID NO. 2:5'-ACCGTTCACCTTGCACTTCTC-3'), which amplified about ~600 bp DNA fragment. The primers for the Gpx1-KO allele were pPNTpgk (SEQ ID NO. 3:5'-CAGTTTCATAGCCTGAAGAACGAGAT-3') and GPX15, which amplified a~200 bp DNA fragment. The primers for the wildtype Gpx2 allele were MPX206 (SEQ ID NO. 4:5'-CCCACCTGTCTAGAGGACTTA-3') and MPXin09 (SEQ ID NO. 5:5'-TCCATGCCAACGTAGTGATT-3'), which amplified a ~600 bp DNA. The primers for the Gpx2-KO allele were MPX206 and pPNTpgk, which amplified a ~400 bp DNA. Both alleles were amplified in the same reaction tubes.

Metabolic Studies

Rectal temperature was measured with Thermalert mouse probe (Model TH-8, Physitemp Instrument Inc., Clifton, N.J.) at the 6–8 am on mice under normal housing. To quantify the food and water consumption and feces and urine output mice were placed in metabolic cages without bedding for 24 h. This setting appeared to be stressful for the double-KO mice, as shown by frequent hunched-over appearance, pilocrection of their coat, and loose stools the next day.

Histology of Small and Large Intestine

Mice were sacrificed by halothane overdose (Halocarbon Labs, North Augusta, S.C.). After removing the lumen contents, sections of jejunum, ileum, colon, and rectum were rinsed with phosphate buffered saline, and then fixed in 10% buffered formalin or Bouin's fixative for 2–3 h. The tissues were then dehydrated in ethanol, and embedded in paraffin and sectioned onto slides. The tissue sections were stained with hematoxylin and eosin (H&E) alone or in addition to periodic acid Schiff (PAS) staining.

GPX Activity Assay

GPX activity was determined on mouse intestinal and colon epithelium. Jejunal and ileal epithelium were isolated from the proximal and the distal one third of small intestine as described previously. Esworthy, R. S., Mann, J. R., Sam, M. & Chu, F. (2000) Am J Physiol Gastrointest Liver Physiol 279, G426–G436. The GPX activity was measured with 60 $\mu$M $H_2O_2$ and 3 mM GSH at pH 7.3. The protein concentration was determined with a BCA assay (Pierce Chemical, Rockford, Ill.) with bovine serum albumin as the standard.

Transgenic animals having a heterozygous or homozygous disruption in one or more genes can also be crossed to other animals having the same or different homozygous or heterozygous disruptions in the same or different genes to generate numerous combinations of heterozygous and homozygous disruptions of multiple genes, as well known in the art and as demonstrated in the Examples of the present invention.

Furthermore, a transgenic animal of the invention can be transformed with a heterologous gene of interest having a disruption in order to modulate the expression of the heterologous gene in an animal having a homozygous disruption of the Gpx1 and Gpx2 genes. In this manner, one can determine the effects of modulating the expression of a heterologous gene of interest on a transgenic animal having a homozygous disruption of the Gpx1 and Gpx2 genes.

As used herein, the term "heterologous gene" or "heterologous nucleic acid sequence" refers to a sequence that originates from a foreign species, or, if from the same species, it may be substantially modified from its original form. The term also encompasses an unchanged nucleic acid sequence that is not normally expressed in a cell. Preferably, the heterologous sequence is operably linked to a promoter, resulting in a chimeric gene. In preferred embodiments, the heterologous gene of interest is associated with either an increase or decrease in at least one sign or symptom of ileitis, colitis, inflammatory bowel disease, ileal cancer and or myeloleukemia. It may also be desirable to observe the effect of a biological response modifier incorporated into the genome of the transgenic animal of the invention. Included in this category are immunopotentiating agents including nucleic acids encoding a number of the cytokines classified as interleukins, interferons, tumor necrosis factor (TNF) tumor suppressor genes, anti-angiogenic genes and the like. See, for example, U.S. Pat. Nos. 6,288,024; 4,879,226; and 6,300,475.

The terms "knockout" and "disruption" each refer to partial or complete reduction of the expression of at least a portion of a nucleic acid or a polypeptide encoded by one or more endogenous genes of a single cell, selected cells, or all of the cells of an animal. The animal may be a "heterozygous knockout" or have a "heterozygous disruption," wherein one allele of one or more endogenous genes have been disrupted. Alternatively, the animal may be a "homozygous knockout" or have a "homozygous disruption," wherein both alleles of one or more endogenous genes have been disrupted.

Methods of generating transgenic mice by inserting a nucleic acid sequence which can cause a disruption in an endogenous gene into the pronuclei of a fertilized mouse oocyte are known in the art (See e.g., U.S. Pat. No. 4,736,866 issued to Leder,et al.). Typically, the sequence is inserted into an undifferentiated cell termed an embryonic stem cell (ES cell). ES cells are usually derived from an embryo or blastocyst of the same species as the developing embryo into which it can be introduced. The knockout sequence can cause a disruption in a gene by insertion of an altered nucleic acid sequence into a homologous region of the coding region of the endogenous nucleic acid sequence (usually containing one or more exons) and/or the promoter region of a gene so as to decrease or prevent expression of the full length gene product in the cell. Insertion is usually accomplished by homologous recombination. Such methods are known in the art. By way of example, a disruption construct can be prepared by inserting, for example, a nucleotide sequence comprising an antibiotic resistance gene into a portion of an isolated nucleotide sequence encoding an endogenous gene that is to be disrupted. When this knockout construct is then inserted into an embryonic stem cell, the construct can integrate into the genomic DNA of at least one allele of the gene. Thus, many progeny of the cell will have the gene disrupted and no longer express the nucleic acid or gene or will express it at a decreased level and/or in a truncated form. Also, use of oligonucleotides or antisense nucleic acids which are complementary to at least a portion of a specific mRNA molecule to stall transcription of the mRNA can also be utilized to disrupt gene expression.

EXAMPLES

The invention is further illustrated by the following examples, which are not intended to be limiting.

Example 1

Generation of Double-KO Mice

Homozygous Gpx1-KO and Gpx2-KO mice were bred to generate heterozygous double-KO mice. These heterozygous double-KO mice were bred to each other, one sixteenth of the offspring were homozygous double-KO mice. One half of mice were reciprocal homozygous and heterozygous KO's, so called 3-quarter KO's. These double-KO and 3-quarter KO were used as breeders to generate the double-KO mice. The genotypes of six mice were analyzed by Southern analysis to examine genetic characteristics of the results of double knockout breeding. Referring now to FIG. 1A, the left panel contains BamHI-digested DNA hybridized with mouse Gpx1 cDNA. The top arrow points at ~11 kb wildtype (WT) allele, and the lower arrow points at ~4.3 kb Gpx1-KO allele. The right panel contains ApaI-digested DNA hybridized with mouse Gpx2 cDNA. The top arrow points at ~14 kb Gpx2 pseudogene (Ps-Gpx2), the middle arrow points at ~7 kb WT allele, and the lowest arrow points at ~4.9 kb Gpx2-KO allele. The other two DNA fragments of low molecular weights do not correlate with Gpx2 genotypes, and are ignored. The genotypes are shown in the bottom of the panels and are designated as follows:+/−, one wildtype and one knockout allele; +/+ two wildtype alleles; −/−, two knockout alleles.

Figure 1B:
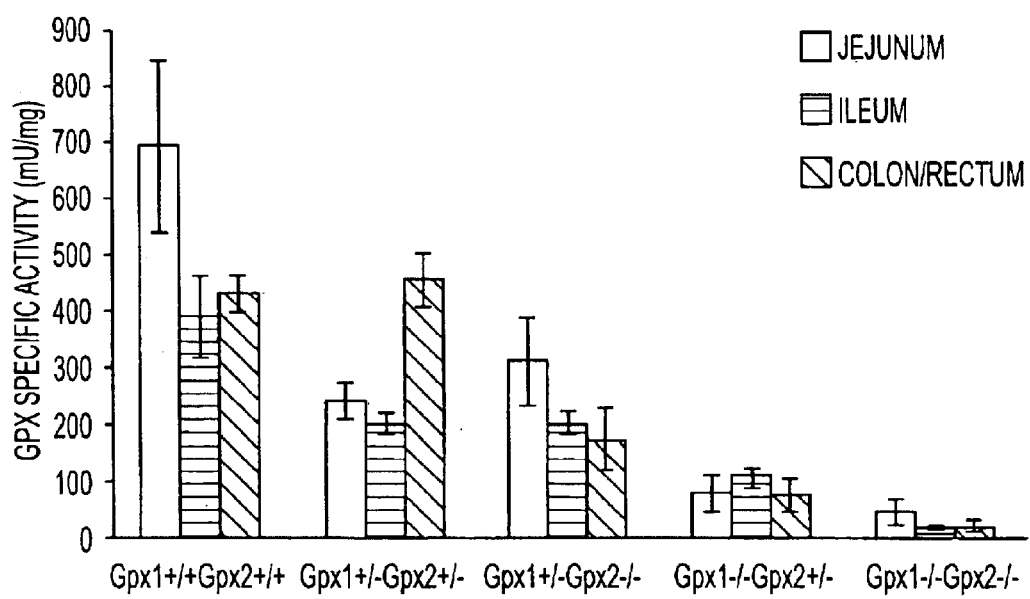
FIG. 1B depicts the results of GPX activity in Gpx1 and Gpx2 double knockout mice compared to non double-KO littermates.

Referring now to FIG. 1B, there are shown the results of GPX enzyme activity in the epithelium of mouse lower GI-tract. GPX activity was measured using hydrogen peroxide as the substrate. The error bars represent variances or standard deviations of the means. The number of mice assayed in each group from left to right is 3, 2, 4, 4, and 4 respectively. The Genotypes for both Gpx1 and Gpx2 are as in 1A.

The number of the double-KO mice was close to the predicted value from Mendelian genetics. Similar numbers of male and female offspring were obtained. This indicates that the double-KO mice have normal embryonic development and there is no gender bias. Both male and female double-KO mice can be fertile but only a small percentage of mice gain enough weight and appear healthy enough to be used as breeders.

Example 2

Growth of Double-KO Mice

Figure 2A:
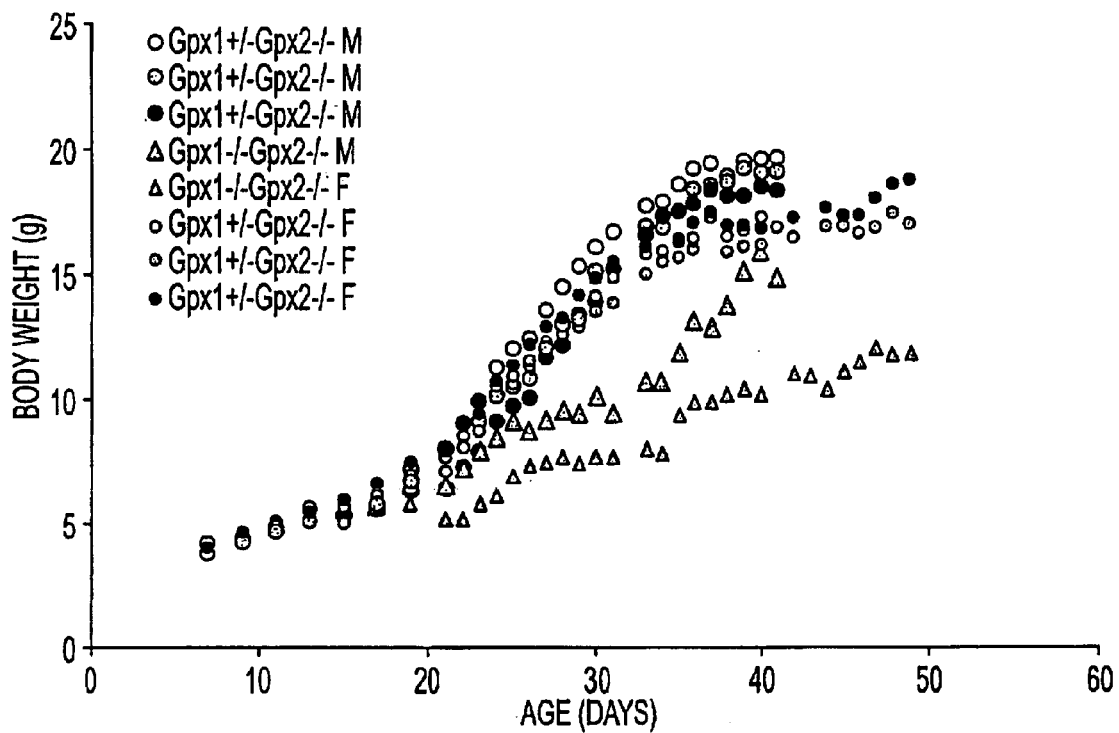
FIG. 2A is a graphical representation of the growth (in body weight) of Gpx1 and Gpx2 homozygous double-KO mice compared with their non double-KO littermates.

Referring now to FIG. 2A, there are shown the results of growth activity in adult (45–47 days old) homozygous double-KO mice. There is shown a graphical representation of the growth rate of a single litter of 8 pups. Male mice are shown in larger symbols, and female mice are shown in smaller symbols. Circles represent Gpx1+/−Gpx2−/−mice, diamonds represent Gpx1−/−Gpx2+/−mice, squares represent Gpx1+/−Gpx2+/−mice, and triangles represent Gpx1−/−Gpx2−/−mice. The female and male double-KO mice in the top panel started to show growth retardation at 21 and 26 days old.

Figure 2B:
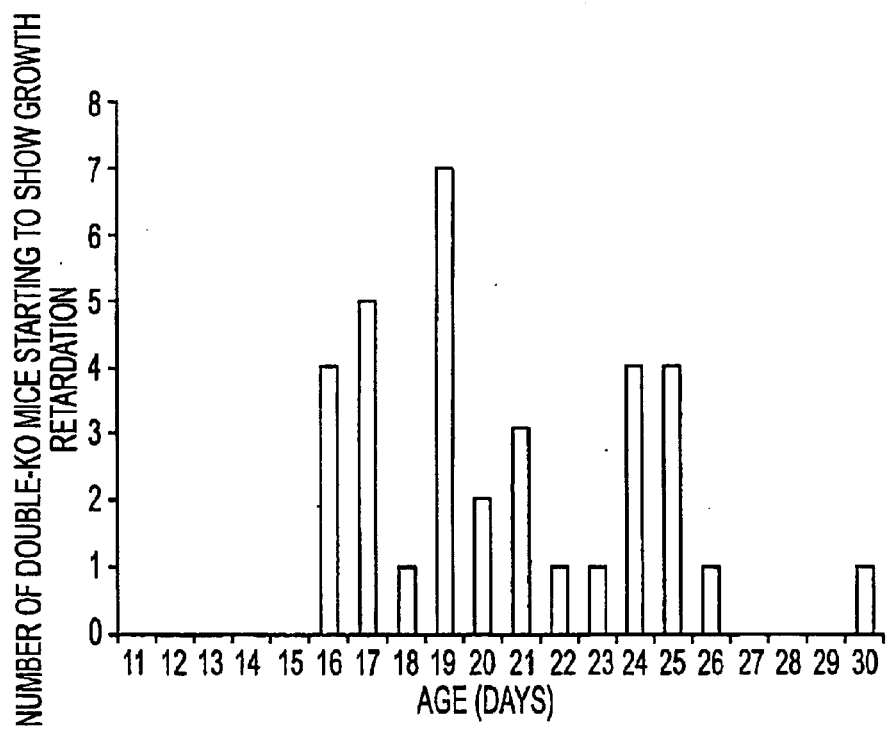
FIG. 2B is a graphical representation of the age at which Gpx1 and Gpx2 homozygous double-KO mice show growth retardation.

Referring now to FIG. 2B, there is shown a graphical representation of the number and age of 33 homozygous double-KO mice at which they first show growth retardation. The double-KO had almost background GPX activity in the mucosa of small and large intestine (Lower Panel of FIG. 1). Since the jejunum mucosa had a high level of GPX-1 and low level of GPX-GI as shown previously (4), the total GPX activity in this region corresponded only to the Gpx1 gene dosage. The GPX-GI contributed little to GPX activity in the jejunum even in a homozygous Gpx1-KO background since the heterozygous and homozygous Gpx2-KO mice do not have statistically different GPX activity (P=0.10) as shown in the last two groups in FIG. 1A. A lower level of GPX-1 and a higher level of GPX-GI are expressed in the ileal mucosa compared with that in jejunal mucosa. The dosage effect of the Gpx2 allele is evident only in the absence of Gpx1 gene expression. In colon mucosa, the heterozygous double-KO has the same level of GPX activity as wildtype mice.

Gross Phenotypes of Double-KO Mice

The homozygous double-KO mice had a slower weight gain compared with mice of other genotypes starting around day 16 postnatally. The two double-KO mice had the same birth weight and maintained the same weight gain as their littermates until weaning. Among the 33 double-KO mice followed, 32 showed growth retardation onset at 16–26 days old. The last one started to show growth retardation at 30 days.

Other symptoms often associated with these homozygous double-KO mice include perianal ulceration (redness and irritation of anal region), anal mucous discharge, and diarrhea. One or more of these symptoms occurred as early as 14 days old. However, most of these symptoms were transient except the perianal ulceration, which appeared to be persistent. Older double-KO transgenic mice, over six months old, had a high level of tumor in the ileum.

The younger homozygous double-KO mice had at least 25% mortality. Death or morbidity indicating imminent death occurred between 20–36 days of age. Five of the 33 homozygous mice that we tracked daily died unexpectedly, three more of the 33 mice were terminated when they appeared moribund judging by persistent weight loss, hunched-over posture, or rectal obstruction. No noticeable abnormality was seen in major organs, for example such the liver, kidney, heart, lung, spleen or lymph nodes in the autopsy.

In spite of the severe growth retardation, wasting syndrome, and mortality, the homozygous double-KO mice had similar weight and length of small and large intestine compared with their littermates up to 25 days old. After 40 days, the length and weight of small intestine in the homozygous double-KO mice began to lag behind their littermates by 20%. However, the weight of colon and rectum in the homozygous double-KO mice was about 20% heavier than that in their littermates. This may simply reflect the thickening of colon mucosa in the double-KO mice.

Example 3

Rectal Hypothermia in Double-KO Mice

Figure 3A:
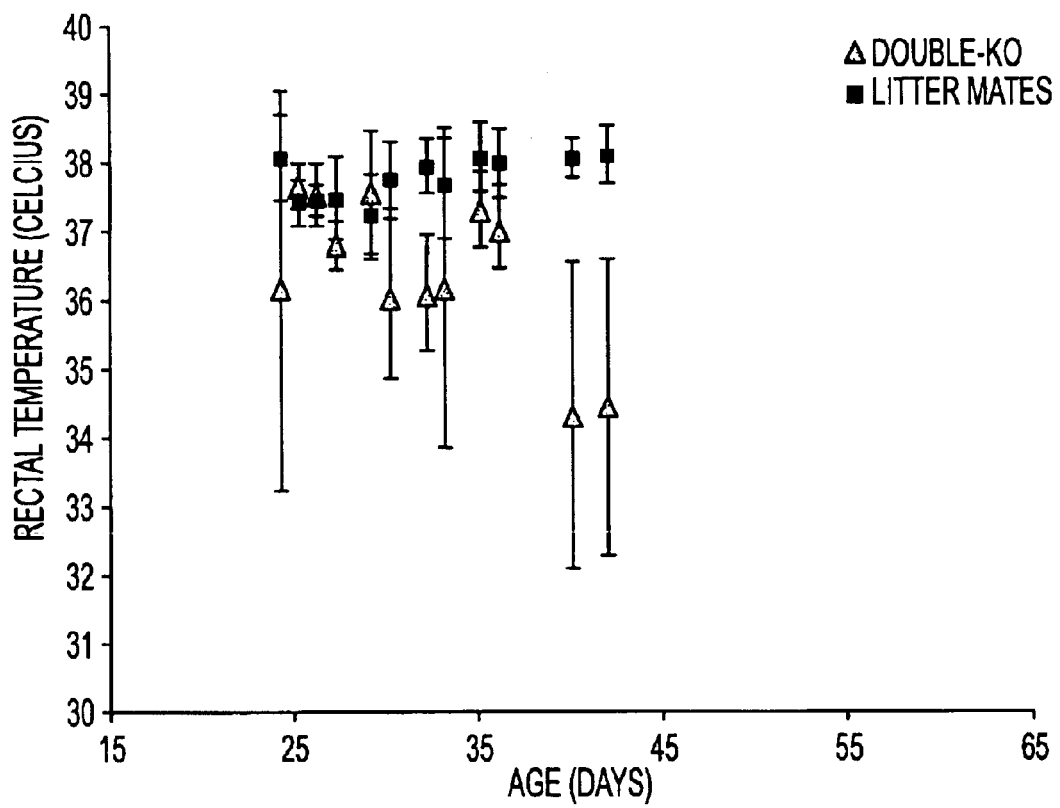
FIG. 3A is a graphical representation of body temperature of Gpx1 and Gpx2 homozygous double-KO mice compared to non-double-KO littermates.
Figure 3B:
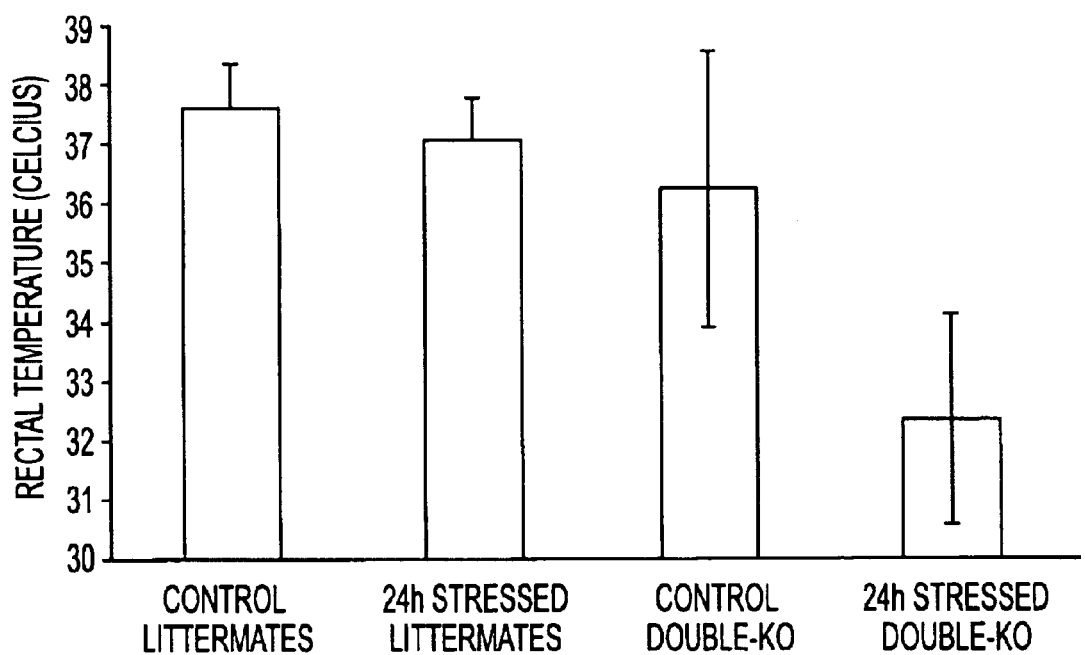
FIG. 3B is a graphical representation of body temperature in response to stress of Gpx1 and Gpx2 homozygous double-KO mice compared to non-double-KO littermates.

To determine if the severe growth retardation was contributed by lack of calorie uptake despite of normal intestinal growth in the homozygous double-KO mice, we monitored the rectal temperature and amount of food uptake by these mice. We found these mice are hypothermic compared with their littermates either under normal housing condition or in metabolic cages where there was no bedding. Referring now to FIG. 3A, there is shown a graphical representation of rectal temperatures of double-KO mice as compared to their littermates. Rectal temperature of homozygous double-KO mice and their littermates with either combined heterozygous KO or three-quarter KO. Double-KO mice are triangles and their littermates are squares. The error bars are variances or standard deviations from means of 2–6 mice. Rectal temperatures of the younger (24–36 days old) and more mature (40–67 days old) double-KO mice were 37.0±1.1° C. and 35.1±2.2° C. respectively. The rectal temperatures of their littermates were 37.6±0.6° C. for all ages under normal housing condition. After being placed in metabolic cages for 24 h, the rectal temperature of 36 day-old double-KO mice had dropped from 36.2±2.3° C. to 32.2±1.8° C. as shown in FIG. 3B. The control mice did not change their rectal temperature significantly after being housed in metabolic cages. The homozygous double-KO mice (24–49 days old) consumed similar amounts of food (0.16±0.07 g mouse chow/g body weight per day, n=11) as their littermates (0.10±0.05 g chow/g body weight per day, n=18). The difference in food intake is not statistically significant. Although the animals had bouts of acute diarrhea and loose stools, they did not have chronic diarrhea.

Referring now to FIG. 3B, there is shown a graphical representation of hypothermia caused by stress in double-KO mice. Adult (36-day-old) mice were stressed by housing singly or doubly in metabolic cages for 24 hours. The error bars are variances of means from four double-KO mice and six littermates with Gpx1+/−Gpx2+/− and Gpx1−/−Gpx2+/− genotypes.

Example 4

Inflammation of the Small Intestine and Colon/Rectum

Figure 4:
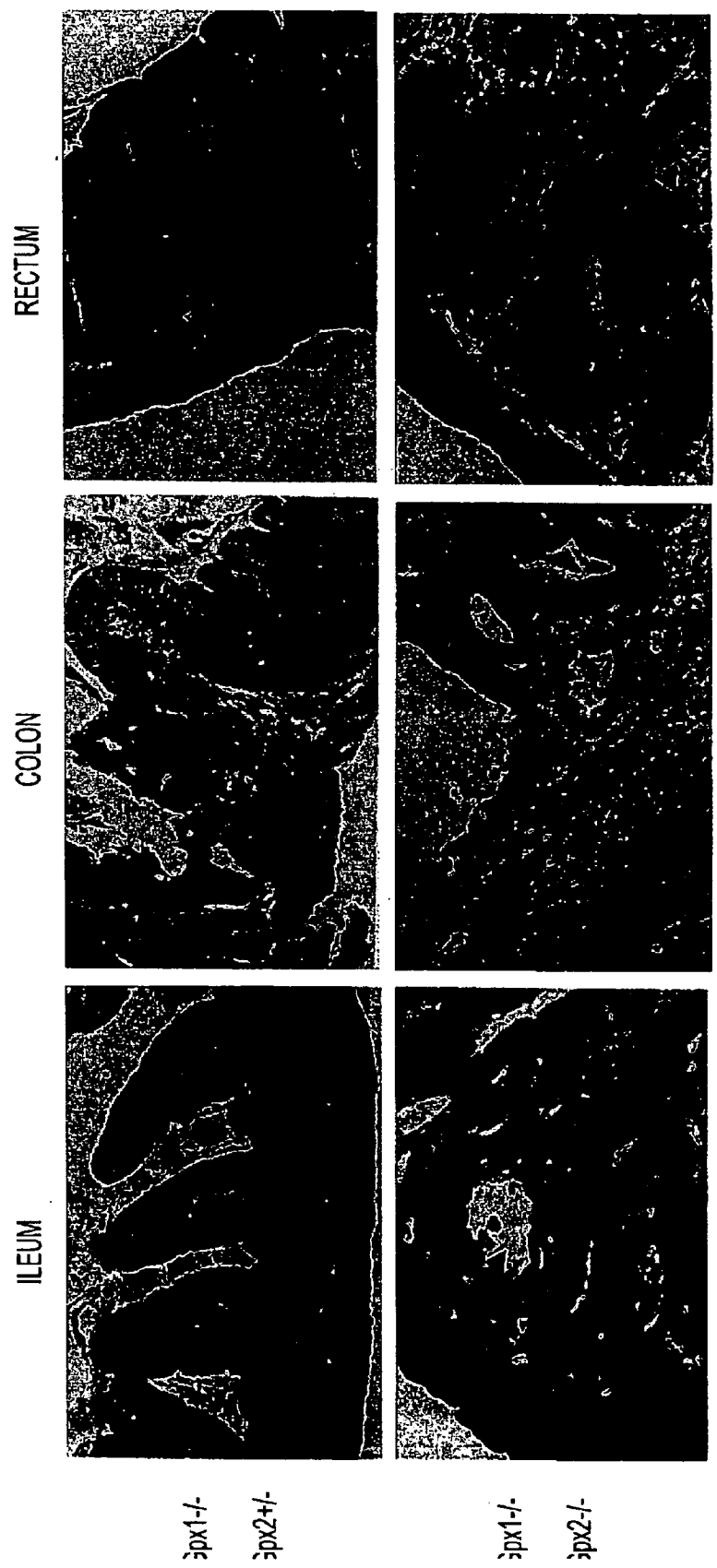
FIG. 4 is a photograph of histological preparations of Gpx1 and Gpx2 homozygous double-KO mice compared to non-double-KO littermates.

Histological analysis was performed on the cross sections of stomach, jejunum, ileum, colon and rectum after staining with hematoxylin and eosin as shown in FIG. 4. Cross sections from two 20 day-old littermates with homozygous double-KO and 3-quarter KO genotypes were compared. The 3-quarter KO had apparent normal histology throughout the GI-tract. In contrast, the double-KO mouse had severe ileitis and colitis, although the jejunum and stomach appeared to be unaffected. Crypt abscesses were prevalent in ileum, colon and rectum.

The extent of ileitis and colitis were scored with the histological changes in five categories: (1) severity of the inflammatory cell infiltrate in lamina propia; (2) epithelial cell reactive hyperplasia/atypia; (3) mucin depletion (colon and rectum only); (4) increases in intraepithelial lymphocyte numbers in crypts; and (5) number of inflammatory foci as defined previously (Aranda, R., Sydora, B. C., McAllister, P.

L., Binder, S. W., Yang, H. Y., Targan, S. R. & Kronenberg, M. (1997) J. Immunol. 158, 3464–73.). Periodic acid Shift (PAS) staining was performed on some sections to confirm the depletion of mucin. Referring now to FIG. 4, there are shown the results of histology of mouse ileum, colon and rectum stained with eosin and hematoxylin. One 3-quarter KO (top row) and one homozygous double-KO (lower row) littermates were sacrificed at 20 days of age. Arrows point at crypt abscesses. The original magnification is 200X.

Table 1 shows the progression of ileitis and colitis from distal to proximal direction in 18 homozygous double-KO mice through early development.

TABLE 1

Severity of inflammation in double-KO mice of the present invention.

| | Age (days) | | | Total no. of mouse |
|---|---|---|---|---|
| | 11–14 | 15–17 | 20–27 | |
| Jejunum[a] | 7N[b] | 3N | 5N | 15 |
| Ileum[a] | 7N | 3N | 4M[b], 4S[b] | 18 |
| Proximal colon[a] | 6N, 1S | 3S | 1N, 2M, 5S | 18 |
| Distal colon[a] | 1N, 3M, 3S | 3S | 2M, 6S | 18 |

[a]jejunum was sampled at 2–4 cm from stomach; ileum was sampled within 2 cm of cecum; proximal colon was taken within 2 cm of cecum; and distal colon was taken within 1–2 cm from anus.
[b]N = normal (with 0–1 scores, the same as control mice); M = mild colitis (with 4.5–7 scores); S = severe (with 8–10 scores). Scoring was based on the 14 point system described by Aranda et al.(33): inflammation (0–3 points), mucin depletion (0–2 points), reactive epithelium (0–3), number of intraepithelial lymphocytes (0–3), inflammatory foci (0–3). No samples were scored in the range of 2–4 or greater than 10.

Spontaneous colitis was shown mostly in the distal colon as early as 11 days of age in 6 out of seven mice analyzed. The proximal colitis was only observed in one of seven 11–14 days old mice analyzed. Most mice of 15 days and older had inflammation in both distal and proximal colon. Ileitis became evident and prevalent in mice of 20–27 days old. No inflammation was seen in the stomach and jejunum in all animals up to 60 days old (Table 1 and other observations). Other major organs including heart, liver, lung, kidney, testis, and brain did not have any noticeable abnormality upon gross and histological analysis.

Example 5
Tumors of the Small Bowel.

Up to 40% of a generation of homozygous double-KO mice with homozygous disruption of Gpx1 and Gpx2 die before 50 days of age. We have found, however, that up to 60% of GPX double KO mice can survive up to 13 months of age. Surviving animals were studied to determine whether impaired peroxide detoxification with concomitant distal gastrointestinal inflammation promoted cancer development.

Many of the mice with homozygous disruption of Gpx1 and Gpx2 exhibited macroscopic tumor located in the distal two-thirds of the small bowel. Homozygous double-KO mice and control mice heterozygous were maintained on a 9% fat chow to prevent wasting and death in the homozygous double-KO mice.

Homozygous double-KO mice that survived past 50 days of age were euthanized at several predetermined discrete time points or alternatively when distress was evident. Following euthanasia, the GI tracts of the mice were observed macroscopically for the presence of gross tumors and also were processed as Swiss Rolls to survey the entire length of the intestine for histological evidence of dysplasia and inflammation. The tumors were similar in histological appearance to human adenocarcinomas.

Figure 5:
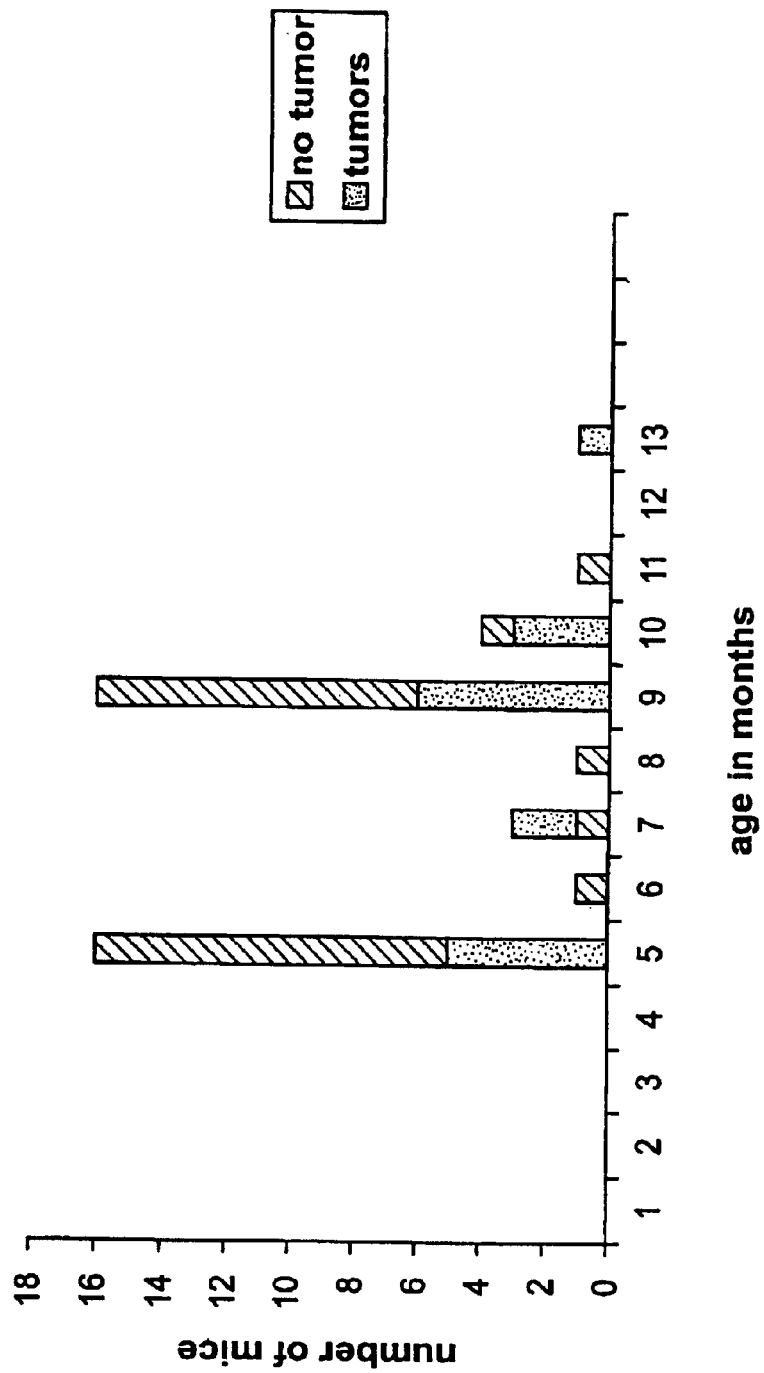
FIG. 5 is a graphical representation of the incidence of tumors in Gpx1 and Gpx2 homozygous double-KO mice as a function of age.

Referring now to FIG. 5, there is shown a graphical representation of the presence of tumors of the small bowel in homozygous double-KO mice having a disruption of the Gpx1 and Gpx2 genes. At five months of age, five of 16 double-KO mice sacrificed had tumors. At 6–8 months, 1 more of 5 additional mice sacrificed had tumors. At 9–13 months, 10 of 21 additional mice sacrificed had tumors. The total number of tumors observed in homozygous double-KO mice having a disruption of the Gpx1 and Gpx2 genes was 16 out of 42 mice that survived to 5 months of age.

Figure 6:
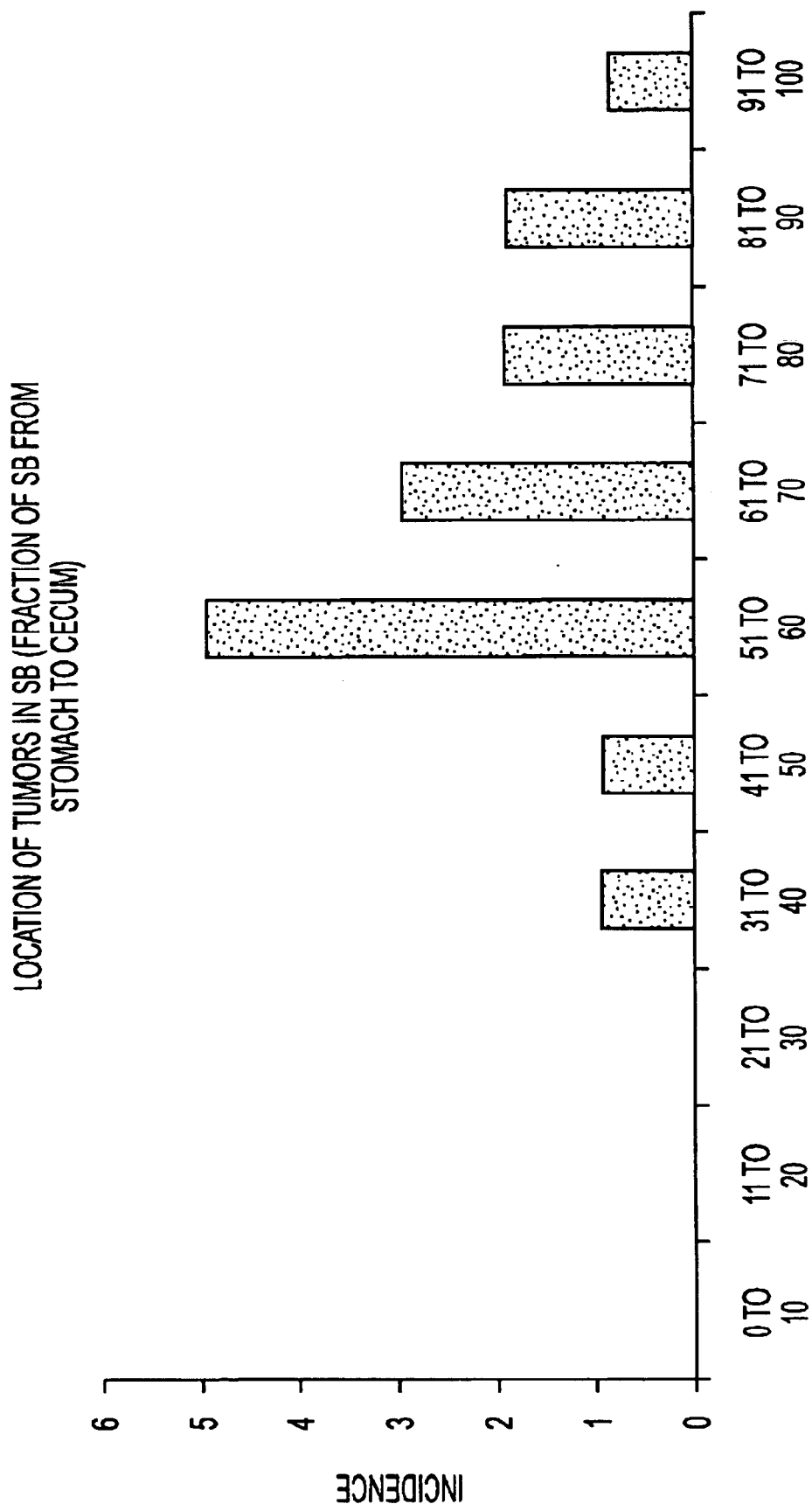
FIG. 6 is a graphical representation of the relative location of tumors in Gpx1 and Gpx2 homozygous double-KO mice.
Figure 7:
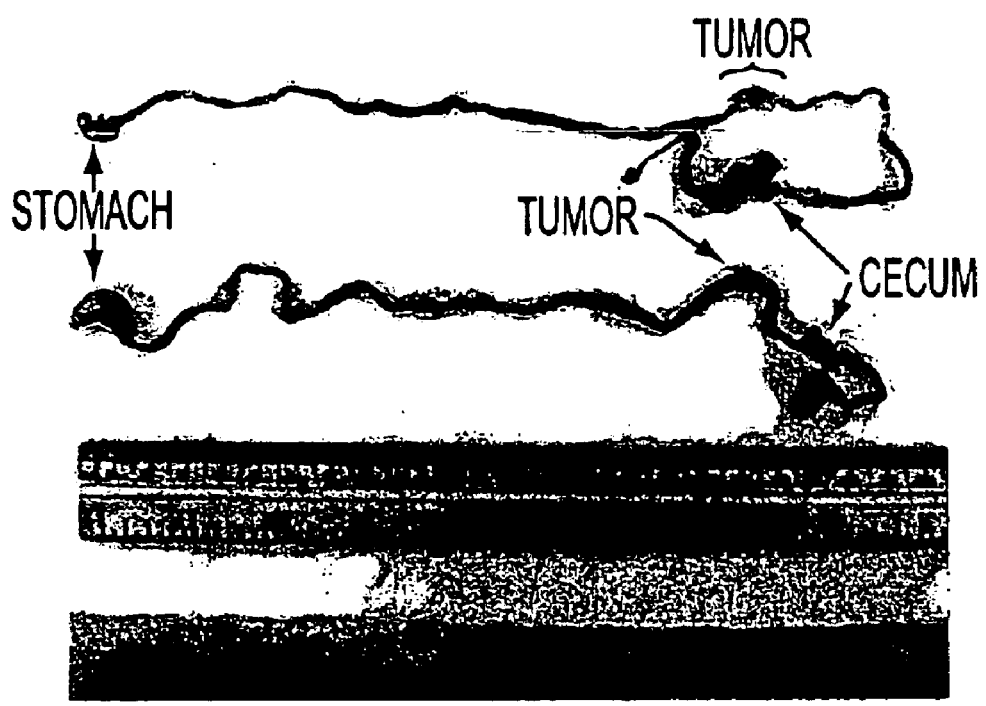
FIG. 7 is a photographic representation of the location of tumors in the small intestine of a Gpx1 and Gpx2 homozygous double-KO mouse.

A total of 23 homozygous double-KO mice were examined according to the above procedures. Eleven (11) of the mice had a macroscopic tumor located in the distal two-thirds of the small bowel. Referring now to FIG. 6 there is shown a graphical representation of the location of tumors and frequency of tumors at precise points along the intestine from the stomach to the cecum. The numbers on the X-axis refer to actual number of mice with tumor at that location. Referring now to FIG. 7, there is shown a photograph depicting two tumors in homozygous double-KO Gpx1/Gpx2 mice and their location the intestine from the stomach to the cecum. Most of these tumors were characterized by a tubular adenomatous pattern that extended over a broad base. In two of the 11 mice showing tumors, neoplastic epithelium had a complex cribiform pattern (back to back glands with no intervening stroma) which was consistent with adenocarcinoma in situ.

In all mice with tumors, no invasion of the tumors into the serosal adipose tissue was observed. Furthermore, none of the homozygous double-KO mice had tumors in the colon. No tumors were detected using the above methods in 25 age-matched control mice. The control mice were either heterozygous for one or both Gpx1 and Gpx2 or homozygous for one or the other of Gpx1 and Gpx2, i.e., control mice were littermates of the double KO mice that were all other combinations resulting from a cross of homozygous Gpx1 and homozygous Gpx2 knockout mice which were not the double knockouts.

Mice with disrupted single Gpx1 and Gpx2 genes are apparently normal. This raises some question as to the individual importance of each of these antioxidant enzymes. This lack of an observable deleterious phenotype in single knockout mice also suggests that animals have overlapping defense system against hydroperoxides, since catalase, glutathione S-transferases and AOP-2 can reduce some species of GPX substrates (Jakoby, W. B. (1985) Methods Enzymol. 113,495–9; 35. Kang, S. W., Chae, H. Z., Seo, M. S., Kim, K., Baines, I. C. & Rhee, S. G. (1998) J. Biol. Chem. 273, 6297–302; Fisher, A. B., Dodia, C., Manevich, Y., Chen, J. W. & Feinstein, S. 1. (1999) J. Biol. Chem. 274, 21326–34; Esworthy, R., Chu, F. F., and Doroshow, J. H. (1999) in Current Protocols in Toxicology, ed. Maines, M., Costa, L., Reed, D., and Sassa, S. (John Wiley & Sons, Inc., pp. 7.1.1–7.1.32). In contrast to the single knockout mice, the gross abnormality found in mice with combined disruption of Gpx1 and Gpx2 genes demonstrates the uniqueness of GPX activity' which cannot be compensated by other types of hydroperoxide-reducing enzymes. This result also suggests that GPX-1 and GPX-GI are functionally redundant.

The GPX-1 appears compensating for lack of GPX-GI in epithelium of small intestine judged by the same level of GPX activity detected in mice expressing 0 and 1 Gpx2 allele. A higher level of GPX-1 in homozygous Gpx2-KO intestine was detected compared to the GPX-1 level in wildtype mice determined by immunoprecipitation (Esworthy et al.(1998) Biochim Biophys Acta 1381,213–26; Esworthy et al. (2000), Am J Physiol Gastrointest Liver Physiol 279, G426–G436). The same level of GPX-GI was detected in Gpx1-KO intestinal mucosa. These observations suggest the Gpx1 gene compensates for lack of Gpx2 gene expression, but not vice versa. The compensation appears to be limited to small intestine but not colon. Alternatively, it is also possible that a part of the expression machinery necessary for selenoproteins in favor of Gpx1 but not Gpx2 gene expression is active in the intestine but not in colon epithelium. This selenoprotein expression machinery includes 3'-untranslated region selenocysteine insertion sequence (SECIS) in mRNA (Gasdaska, J. R., Harney, J. W., Gasdaska, P. Y., Powis, G. & Berry, M. J. (1999) J Biol Chem 274, 25379–25385), selenocysteine tRNA$^{[ser]Sec}$ (Moustafa, M. E., El-Saadani, M. A., Kandeel, K. M., Mansur, D. B., Lee, B. J., Hatfield, D. L. & Diamond, A. M. (1998) RNA 4,1436–43), a SECIS binding protein named SBP2 (Copeland, P. R. & Driscoll, D. M. (1999) J Biol Chem 274, 25447–54; Copeland, P. R., Fletcher, J. E., Carlson, B. A., Hatfield, D. L. & Driscoll, D. M. (2000) Embo J 19, 306–314), and mammalian Upf1 protein (also known as Rent or regulator of nonsense transcripts) (Sun, X., Perlick, H. A., Dietz, H. C. & Maquat, L. E. (1998) Proc. Natl. Acad. Sci. USA 95,10009–14), etc. It is not clear if any of these factors differentiate between Gpx1 and Gpx2 mRNAs. The same GPX level in colon mucosa of wildtype control and heterozygous double-KO mice suggests that this expression machinery for selenoproteins may be a limiting factor.

It is clear that the double-KO mice have almost no GPX activity in the mucosa of distal GI-tract. Although 3-quarter KO mice with no Gpx1 alleles have only a small fraction of total GPX activity in the distal GI-tract, this low level of activity appears to sufficient to maintain normal physiology. In fact, rodent GI-epithelium may have one-fold higher GPX activity compared with that in humans. The specific activity of GPX in human intestine and colon mucosa is 100–240 mU/mg protein compared with 300–700 mU/mg in rats (4) and mice. Although the difference in GPX activity level in the GI-tract is not as big as that in liver, where humans have 352±89 mU/mg (Esworthy, R. S., Baker, M. A. & Chu, F. F. (1995) Cancer Res 55, 957–62) and rodents have ~4,000 mU/mg (44. Chu, F. F., Esworthy, R. S., Ho, Y. S., Bermeister, M., Swiderek, K. & Elliott, R. W. (1997) Biomed Environ Sci 10, 156–62; Esworthy, R. S., Ho, Y. S. & Chu, F. F. (1997) Arch Biochem Biophys 340, 59–63.), the lower GPX activity level in human GI-tract suggests its higher susceptibility to peroxidative injury.

The first sign of abnormality observed in these double-KO mice is growth retardation. It is well documented that severe Se-deficiency causes growth retardation in young animals (Thompson, K. M., Haibach, H., Evenson, J. K. & Sunde, R. A. (1998) J Nutr. 128, 1289–95). Injection of triiodothyronine ($T_3$) to restore plasma thyroid levels in these Se-deficient animals did not increase animal weight gain (Thompson, K. M., Haibach, H. & Sunde, R. A. (1995) J. Nutr. 125, 864–73). Since GPXs are Se-dependent enzymes, this slow growth caused by Se-deficiency in $2^{nd}$ generation rodents can be explained by lack of GPX-1 and GPX-GI in the GI-tract. This suggests that these $2^{nd}$ generation Se-deficient animals should be examined for colitis. To determine if growth retardation in the homozygous double-KO mice is due to lack of food intake, mice were placed in metabolic cages to monitor the amount of food, water and excretion for a 24-hour period. Often, two mice were placed in one metabolic cage since the double-KO mice could not sustain the stress well when housed alone in this setting. The stress may be contributed by the cooler air due to lack of bedding and shelter. Since the double-KO mice consume the same amount of food as their littermates, and do not have chronic osmotic diarrhea, it is possible that these double-KO mice are either deficient in converting the calorie intake into metabolic fuel as implicated in the older Gpx1-KO mice Esposito, L. A., Kokoszka, J. E., Waymire, K. G., Cottrell, B., MacGregor, G. R. & Wallace, D.C. (2000) Free Radic Biol Med 28, 754–66, or suffering from inflammation-induced cachexia(Liu, Z., Geboes, K., Colpaert, S., Overbergh, L., Mathieu, C., Heremans, H., de Boer, M., Boon, L., DHaens, G., Rutgeerts, P. & Ceuppens, J. L. (2000) J Immunol 164, 6005–14.

Many mammals respond to energy deficit, such as calorie restriction, by lowering body temperature (Lane, M. A., Baer, D. J., Rumpler, W. V., Weindruch, R., Ingram, D. K., Tilmont, E. M., Cutler, R. G. & Roth, G. S. (1996) Proc Natl Acad Sci USA 93, 4159–64). In fact, fasting can induce torpor or extreme hypothermia in mice (Gavrilova, O., Leon, L. R., Marcus-Samuels, B., Mason, M. M., Castle, A. L., Refetoff, S., Vinson, C. & Reitman, M. L. (1999) Proc.Natl.Acad.Sci. USA 96,14623–8). Since these mice have wasting syndrome, we wanted to determine if they also have hypothermia consistent with deprivation in metabolic energy. The hypothermia presented in these mice support the notion that these mice may not be getting enough calories despite unrestricted access to food and normal appetite. It will readily be appreciated by those skilled in the art that determination of hypothermia in mice of the present invention supplied with a high fat diet can be utilized to answer this question.

Animals suffering from inflammatory bowel disease (IBD) often show wasting (Aranda, R., Sydora, B. C., McAllister, P. L., Binder, S. W., Yang, H. Y., Targan, S. R. & Kronenberg, M. (1997) J. Immunol. 158, 3464–73). The double-KO mice tend to have colon inflammation, which shows up as a thickened colon and heavier colon weight. Panwala, C. M., Jones, J. C. & Viney, J. L. (1998) J Immunol 161, 5733–44. Histological study shows that these homozygous double-KO mice have spontaneous inflammation starting from distal colon as early as 11 days old, which was the youngest age analyzed. Inflammation progresses from distal colon to proximal colon and then to ileum. The increased severity in colonic inflammation around weaning appears to be correlated with the increased number of species of colonic bacteria Madsen, K. L., Doyle, J. S., Tavemini, M. M., Jewell, L. D., Rennie, R. P. & Fedorak, R. N. (2000) Gastroenterology 118, 1094–105. The alteration in colonic bacterial flora can result from either ingestion of solid food which alters luminal pH (Hentges, D. J., Marsh, W. W., Petschow, B. W., Thai, W. R. & Carter, M. K. (1992) J. Pediatr. Gastroenterol. Nutr. 14, 146–52) or decreased in the protective IgA and other bactericidal components present in milk(Orlando, S. (1995) J Obstet Gynecol Neonatal Nurs 24, 678–83). The severity and timing of ileitis and colitis in these double-KO mice is consistent with the notion that microflora is an important cofactor in the pathogenesis of colonic inflammation (Panwala, C. M., Jones, J. C. & Viney, J. L. (1998) J Immunol 161, 5733–44; Madsen, K. L., Doyle, J. S., Tavemini, M. M., Jewell, L. D., Rennie, R. P. & Fedorak, R. N. (2000) Gastroenterology 118, 1094–105.). Germ free mice of the present invention can be utilized to make this analysis.

Reactive oxygen species have been implicated in the pathogenesis of IBD. The inflamed colon has elevated levels of oxygen metabolites detected by chemiluminescence (Simmonds, N. J., Allen, R. E., Stevens, T. R., Van Someren, R. N., Blake, D. R. & Rampton, U. S. (1992) Gastroenterology 103, 186–96; Keshavarzian, A., Sedghi, S., Kanofsky, J., List, T., Robinson, C., Ibrahim, C. & Winship, D. (1992) Gastroenterology 103,177–85). Catalase, superoxide dismutase, or azide(a myoleperoxidase inhibitor) decreases chemiluminescence. Compounds used for IBD therapy such as 5-aniinosalicylates have antioxidant activity (26; Nfillar, A. D., Rampton, D. S., Chander, C. L., Claxson, A. W., Blades, S., Coumbe, A., Panetta, J., Morfis, C. J. & Blake, D. R. (1996) Gut 39,407–15). Thus, increased oxidative stress may play an important role in the pathogenesis of IBD. Selenium deficiency is common in those patients with severe gastrointestinal disorders due to impaired intestinal absorption (Rannem, T., Ladefoged, K., Hylander, E., Hegnhoj, J. & Jarnum, S. (1992) Am. J. Clin. Nutr. 56, 933–7;32; Rannem, T., Ladefoged, K., Hylander, E., Hegnhoj, J. & Staun, M. (1998) Scand. J. Gastroenterol 33, 1057–61). However, little evidence supports the role of GPX in pathogenesis of IBD. Thus, the IBD phenotypes presented in these double-KO mice provide the first evidence to link GPX activity with this disease affecting one million Americans.

Inflammatory Bowel Disease is associated with an increased overall risk for colon and small intestine carcinoma. (Cancer risk is related to disease duration increasing 0.5–1% per year.) Rectal carcinoma risk is increased 2 fold in patients with ulcerative colitis and there is a huge increase in risk for small intestine carcinoma (17 fold) in Crohn's Disease patients. See e.g., Pohl et al., Hepatogastroenterology, 47(31):57–70 (2000) and Bernstein et al., Cancer 91:854–862 (2001). The appearance of dysplasia over large areas precedes adenoma and carcinoma in both humans and Gpx1/Gpx2 double knockout mice. The Gpx1/Gpx2 double knockout mice are thus a model for the significant risk of small intestine carcinoma associated with Crohn's disease with regards to precancerous lesions, dysplasia over large areas and dramatic increase in risk for tumors and carcinomas of the small intestine. The Gpx1/Gpx2 double knockout mice of the present invention also develop myeloleukemia and thus present a useful model for this disease also.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

References

1. Ursini, F., Heim, S., Kiess, M., Maiorino, M., Roveri, A., Wissing, J. & Flohe, L. (1999) Science 285, 1393–6.
2. Chu, F. F. (1994) Cytogenet Cell Genet 66, 96–8.
3. Chu, F. F., Doroshow, J. H. & Esworthy, R. S. (1993) J Biol Chem 268, 2571–6.
4. Esworthy, R. S., Swiderek, K. M., Ho, Y. S. & Chu, F. F. (1998) Biochim Biophys Acta 1381,213–26.
5. Tham, D. M., Whitin, J. C., Kim, K. K., Zhu, S. X. & Cohen, H. J. (1998) Am J Physiol 275, G1463–71.
6. Kim, K. K., Whitin, J. C., Sukhova, N. M. & Cohen, H. J. (1999) Pediatr Res 46, 715–21.
7. Roveri, A., Casasco, A., Maiorino, M., Dalan, P., Cafligaro, A. & Ursini, F. (1992) J Biol Chem 267, 6142–6.
8. Chu, F. F. & Esworthy, R. S. (1995) Arch Biochem Biophys 323, 288–94.
9. Thomas, J. P., Maiorino, M., Ursini, F. & Girotti, A. W. (1990) J Biol Chem 265, 454–61.
10. Esworthy, R. S., Chu, F. F., Geiger, P., Girotti, A. W. & Doroshow, J. H. (1993) Arch Biochem Biophys 307, 29–34.
11. Ho, Y. S., Magnenat, J. L., Bronson, R. T., Cao, J., Gargano, M., Sugawara, M. & Funk, C. D. (1997) J Biol Chem 272, 16644–51.
12. Esposito, L. A., Kokoszka, J. E., Waymire, K. G., Cottrell, B., MacGregor, G. R. & Wallace, D.C. (2000) Free Radic Biol Med 28, 754–66.
13. Esworthy, R. S., Mann, J. R., Sam, M. & Chu, F. (2000) Am J Physiol Gastrointest Liver Physiol 279, G426–G436.
14. Cheng, W. H., Ho, Y. S., Valentine, B. A., Ross, D. A., Combs, G. F., Jr. & Lei, X. G. (1998) J. Nutr 128,1070–6.
15. de Haan, J. B., Bladier, C., Griffiths, P., Kelner, M., O'Shea, R. D., Cheung, N. S., Bronson, R. T., Silvestro, M. J., Wild, S., Zheng, S. S., Beart, P. M., Hertzog, P. J. & Kola, 1. (1998) J Biol Chem 273, 22528–36.
16. Klivenyi, P., Andreassen, 0. A., Ferrante, R. J., Dedeoglu, A., Mueller, G., Lancelot, E., Bogdanov, M., Andersen, J. K., Jiang, D. & Beal, M. F. (2000) J Neurosci 20, 1–7.
17. Tipton, K. F. & Singer, T. P. (1993) J Neurochem 61, 1191–206.
18. Mirochnitchenko, O., Palnitkar, U., Philbert, M. & Inouye, M. (1995) Proc Natl Acad Sci USA 92, 8120–4.
19. Jiang, D., Akopian, G., Ho, Y. S., Walsh, J. P. & Andersen, J. K. (2000) Exp Neurol 164, 257–68.
20. Lu, Y. P., Lou, Y. R., Yen, P., Newmark, H. L., Nfirochnitchenko, 0. I., Inouye, M. & Huang, M. T. (1997) Cancer Res 57, 1468–74.
21. Jaeschke, H., Ho, Y. S., Fisher, M. A., Lawson, J. A. & Farhood, A. (1999) Hepatology 29,443–50.
22. Beck, M. A., Esworthy, R. S., Ho, Y. S. & Chu, F. F. (1998) Faseb J 12,1143–9.
23. Chu, F. F., Esworthy, R. S., Lee, L. & Wilczynski, S. (1999) J Nutr 129, 1846–1854.
24. Panwala, C. M., Jones, J. C. & Viney, J. L. (1998) J Immunol 161, 5733–44.
25. Madsen, K. L., Doyle, J. S., Tavemini, M. M., Jewell, L. D., Rennie, R. P. & Fedorak, R. N. (2000) Gastroenterology 118, 1094–105.
26. Sands, B. E. (2000) Gastroenterology 118, S68–82.
27. Simmonds, N. J., Allen, R. E., Stevens, T. R., Van Someren, R. N., Blake, D. R. & Rampton, U. S. (1992) Gastroenterology 103, 186–96.
28. Keshavarzian, A., Sedghi, S., Kanofsky, J., List, T., Robinson, C., Ibrahim, C. & Winship, D. (1992) Gastroenterology 103,177–85.
29. Thomas, A. G., Miller, V., Shenkin, A., Fell, G. S. & Taylor, F. (1994) J Pediatr Gastroenterot Nutr 19, 213–9.
30. Hoffenberg, E. I., Deutsch, J., Smith, S. & Sokol, R. J. (1997) Am J Clin Nutr 65, 1482–8.
31. Rannem, T., Ladefoged, K., Hylander, E., Hegnhoj, J. & Jarnum, S. (1992) Am J Clin. Nutr 56, 933–7.
32. Rannem, T., Ladefoged, K., Hylander, E., Hegnhoj, J. & Staun, M. (1998) Scand J Gastroenterol 33, 1057–61.
33. Aranda, R., Sydora, B. C., McAllister, P. L., Binder, S. W., Yang, H. Y., Targan, S. R. & Kronenberg, M. (1997) J Immunol 158, 3464–73.
34. Esworthy et al., Am. J. Physiol.Gastrointest. Liver Physiol. 281:G848–855 (2001) 35.
35. Pinczower, et al., J. Cancer 54(3) 391–396 (1993).
36. Gradagni et al., Cancer Res. 61, 2523–2536.
37. Gauthier et al., Br. J. Cancer 84(5) 631–635 (2001)
38. Jakoby, W. B. (1985) Methods Enzymol 113,495–9.
39. Kang, S. W., Chae, H. Z., Seo, M. S., Kim, K., Baines, I. C. & Rhee, S. G. (1998) J Biol Chem 273, 6297–302.

40. Fisher, A. B., Dodia, C., Manevich, Y., Chen, J. W. & Feinstein, S. 1. (1999) J Biol Chem 274, 21326–34.
41. Esworthy, R., Chu, F. F., and Doroshow, J. H. (1999) in Current Protocols in Toxicology, ed. Maines, M., Costa, L., Reed, D., and Sassa, S. (John Wiley & Sons, Inc., pp. 7.1.1–7.1.32.
42. Gasdaska, J. R., Hamey, J. W., Gasdaska, P. Y., Powis, G. & Berry, M. J. (1999) J Biol Chem 274, 25379–25385.
43. Moustafa, M. E., El-Saadani, M. A., Kandeel, K. M., Mansur, D. B., Lee, B. J., Hatfield, D. L. & Diamond, A. M. (1998) RNA 4,1436–43.
44. Copeland, P. R. & Driscoll, D. M. (1999) J Biol Chem 274, 25447–54.
45. Copeland, P. R., Fletcher, J. E., Carlson, B. A., Hatfield, D. L. & Driscoll, D. M. (2000) Embo J 19, 306–314.
46. Sun, X., Perlick, H. A., Dietz, H. C. & Maquat, L. E. (1998) Proc Natl Acad Sci U S A 95,10009–14.
47. Esworthy, R. S., Baker, M. A. & Chu, F. F. (1995) Cancer Res 55, 957–62.
48. Chu, F. F., Esworthy, R. S., Ho, Y. S., Bermeister, M., Swiderek, K. & Elliott, R. W. (1997) Biomed Environ Sci 10, 156–62.
49. Esworthy, R. S., Ho, Y. S. & Chu, F. F. (1997) Arch Biochem Biophys 340, 59–63.
50. Thompson, K. M., Haibach, H., Evenson, J. K. & Sunde, R. A. (1998) J Nutr 128, 1289–95.
51. Thompson, K. M., Haibach, H. & Sunde, R. A. (1995) J Nutr 125, 864–73.
52. Liu, Z., Geboes, K., Colpaert, S., Overbergh, L., Mathieu, C., Heremans, H., de Boer, M., Boon, L., DHaens, G., Rutgeerts, P. & Ceuppens, J. L. (2000) J Immunol 164, 6005–14.
53. Lane, M. A., Baer, D. J., Rumpler, W. V., Weindruch, R., Ingram, D. K., Tilmont, E. M., Cutler, R. G. & Roth, G. S. (1996) Proc Natl Acad Sci USA 93, 4159–64.
54. Gavrilova, O., Leon, L. R., Marcus-Samuels, B., Mason, M. M., Castle, A. L., Refetoff, S., Vinson, C. & Reitman, M. L. (1999) Proc NatlAcadSci USA 96,14623–8.
55. Hentges, D. J., Marsh, W. W., Petschow, B. W., Thai, W. R. & Carter, M. K. (1992) J Pediatr Gastroenterol Nutr 14, 146–52.
56. Orlando, S. (1995) J Obstet Gynecol Neonatal Nurs 24, 678–83.
57. Nfillar, A. D., Rampton, D. S., Chander, C. L., Claxson, A. W., Blades, S., Coumbe,
58. A., Panetta, J., Morfis, C. J. & Blake, D. R. (1996) Gut 39,407–15.
59. Pohl et al., Hepatogastroenterology, 47(31):57–70 (2000)
60. Bernstein et al., Cancer 91:854–862 (2001).

What is claimed is:

1. A transgenic double knockout mouse whose genome contains a homozygous disruption of both the endogenous Gpx1 gene and Gpx2 gene, wherein said transgenic mouse exhibits one or more physiological symptoms selected from the group consisting of ileitis, colitis, hypothermia, decreased rate of weight pain, perianal ulceration, diarrhea, wasting syndrome, inflammatory bowel disease, one or more tumors in the small bowel and cancer of the small intestine.

2. A cell from the transgenic mouse of claim 1.

3. A cell of claim 2 which is selected from the group consisting of stem cells, epithelial cells and myelofibroblasts.

4. The transgenic mouse of claim 1 wherein the genetic background of the mouse is selected from the group consisting of a B6 mouse, a 129Sv/J hybrid mouse, a 129S3 hybrid mouse and a ½ B6, ¼ 129Sv/J and ¼ 129S3 hybrid mouse.

5. A transgenic mouse as in claim 1 which further comprises a mouse which is a germ free mouse.

6. A transgenic double knockout mouse as in claim 1 whose genome comprises a homozygous disruption of the endogenous Gpx1 gene and a homozygous disruption of the endogenous Gpx2 gene, wherein each disruption comprises the insertion of a transgene.

7. A cell isolated from a double knockout mouse as in claim 6.

8. A cell as in claim 7, selected from the group consisting of a stem cell, an epithelial cell and a myofibroblast.

9. A cell as in claim 8 which is a stem cell.

10. A cell as in claim 8 which is an epithelial cell.

11. A cell as in claim 8 which is a myofibroblast.

12. A transgenic double knockout mouse as in claim 6 which further comprises a mouse which is a germ free mouse.

13. A transgenic double knockout mouse as in claim 1 wherein said knockout mouse is a mouse with a B6 genetic background.

14. A transgenic double knockout mouse as in claim 1 wherein said knockout mouse is a hybrid mouse having a ½ B6, ¼ 129 SuJ and ¼ 129 S3 genetic background.

\* \* \* \* \*